US009834615B2

(12) United States Patent
Fischer et al.

(10) Patent No.: US 9,834,615 B2
(45) Date of Patent: Dec. 5, 2017

(54) METHODS FOR THE GENERATION OF MULTISPECIFIC AND MULTIVALENT ANTIBODIES

(75) Inventors: Nicolas Fischer, Geneva (CH); Giovanni Magistrelli, Cessy (FR); Franck Gueneau, Saint-Julien-en-Genevois (FR); Ulla Ravn, Geneva (CH); Greg Elson, Collonges Sous Saleve (FR)

(73) Assignee: NOVIMMUNE SA (CH)

( * ) Notice: Subject to any disclaimer, the term of this patent is extended or adjusted under 35 U.S.C. 154(b) by 0 days.

(21) Appl. No.: 13/210,723

(22) Filed: Aug. 16, 2011

(65) Prior Publication Data

US 2012/0184716 A1 Jul. 19, 2012

Related U.S. Application Data

(60) Provisional application No. 61/374,159, filed on Aug. 16, 2010, provisional application No. 61/443,008, filed on Feb. 15, 2011, provisional application No. 61/509,260, filed on Jul. 19, 2011.

(51) Int. Cl.
| | | |
|---|---|---|
| *C07K 16/46* | (2006.01) | |
| *C07K 16/00* | (2006.01) | |
| *C07K 16/24* | (2006.01) | |
| *C07K 16/28* | (2006.01) | |
| *C12N 15/10* | (2006.01) | |

(52) U.S. Cl.
CPC .......... *C07K 16/468* (2013.01); *C07K 16/005* (2013.01); *C07K 16/248* (2013.01); *C07K 16/249* (2013.01); *C07K 16/2866* (2013.01); *C12N 15/1037* (2013.01); *C12N 15/1075* (2013.01); *C07K 2317/31* (2013.01); *C07K 2317/32* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| 8,642,745 B2 | 2/2014 | Arathoon et al. |
| 2003/0207346 A1 | 11/2003 | Arathoon et al. |
| 2005/0266425 A1* | 12/2005 | Zauderer et al. ........... 435/6 |
| 2007/0031422 A1* | 2/2007 | McGrew et al. ........ 424/146.1 |
| 2007/0098712 A1 | 5/2007 | Arathoon et al. |

FOREIGN PATENT DOCUMENTS

| GB | 2197322 A | 5/1988 |
| GB | 2197323 A | 5/1988 |
| JP | 2001/523971 | 11/2001 |
| JP | 2006/515503 | 6/2006 |
| JP | 2009/511892 | 3/2009 |
| JP | 2009/541275 | 11/2009 |
| WO | WO 91/04336 A1 | 4/1991 |
| WO | WO 2006/066171 A1 | 6/2006 |
| WO | WO 2009/008253 A1 | 7/2009 |
| WO | WO 2009/149185 A2 | 12/2009 |
| WO | WO-2010135558 A1 | 11/2010 |

OTHER PUBLICATIONS

Mariuzza et al. (Annu. Rev. Biophys. Biophys. Chem. 1987; 16: 139-159).*
Bostrom et al. (Science, 323: 1610-1614, 2009).*
Ravn et al., "By-passing in vitro screening—next generation sequencing technologies applied to antibody display and in silico candidate selection." Nucleic Acids Research, vol. 38(21): e193 (2010).
Bostrom et al. "Variants of the Antibody Herceptin That Interact with HER2 and VEGF at the Antigen Binding Site" (Science, 323: 1610-1614, 2009).
Davis JH et al., 2010, "SEEDbodies: fusion proteins based on strand-exchange engineered domain (SEED) CH3 heterodimers in an Fc analogue platform for asymmetric binders or immunofusions and bispecific antibodies" PEDS 23:195-202.
Demanet et al., "Bispecific Antibody-Mediated Immunotherapy of the BCL, Lymphoma Increased Efficacy With Multiple Injections and CD28-Induced Costimulation." Blood 1996; 87: 4390-4398.
Dreier T et al., "Extremely Potent, Rapid and Costimulation-Independent Cytotoxic T-Cell Response Against Lymphoma Cells Catalyzed by a Single-Chain Bispecific Antibody." Int J Cancer 2002; 100:690-697.
Fagete S. et al. "Specificity tuning of antibody fragments to neutralize two human chemokines with a single agent", Mabs Landes Bioscience, US, vol. 1, No. 3, Apr. 7, 2009, pp. 288-296.
Fischer N. "New magic bullets can hit more than one target", Expert Opinion on Drug Discovery, Informa Healthcare, London, GB, vol. 3, No. 8, Jan. 1, 2008, pp. 833-839.

(Continued)

*Primary Examiner* — Brad Duffy
*Assistant Examiner* — Nelson B Moseley, II
(74) *Attorney, Agent, or Firm* — Cooley LLP; Ivor Elrifi; Cynthia Kozakiewicz

(57) ABSTRACT

The invention provides novel bispecific monoclonal antibodies carrying a different specificity for each binding site of the immunoglobulin molecule and methods for producing novel bispecific monoclonal antibodies carrying a different specificity for each binding site of the immunoglobulin molecule. The antibodies are composed of a single heavy chain and two different light chains, one containing a Kappa constant domain and the other of a Lambda constant domain. The invention provides methods for the isolation of antibodies of different specificities but sharing a common heavy chain. The invention also provides methods for the controlled co-expression of two light chains and a single heavy chain leading to the assembly of monospecific and bispecific antibodies. The invention provides a mean of producing a fully human bispecific and bivalent antibody that is unaltered in sequence and does not involve the use of linkers or other non-human sequences, as well as antibody mixtures of two monospecific antibodies and one bispecific antibody. The invention also provides the means of efficiently purifying the bispecific antibody.

2 Claims, 28 Drawing Sheets

(56) References Cited

OTHER PUBLICATIONS

Fischer N. et al. "Bispecific antibodies: Molecules that enable novel therapeutic strategies", Pathobiology, vol. 74, No. 1, May 1, 2007, pp. 3-14.
Gu et al. "Rationale and development of multispecific antibody drugs." Expert Review of Clinical Pharmacology, vol. 3(4): 491-508 (2010).
Goldstein J et al., "Cytolytic and Cytostatic Properties of an Anti-Human FcγRI (CD64) X Epidermal Growth Factor Bispecific Fusion Protein." J Immunol 1997; 158: 872-879.
Kipriyanov SM. "Generation and Characterization of Bispecific Tandem Diabodies for Tumor Therapy." Methods Mol Biol 2003; 207:323-333.
Lu D et al., "A Fully Human Recombinant IgG-like Bispecific Antibody to Both the Epidermal Growth Factor Receptor and the Insulin-like Growth Factor Receptor for Enhanced Antitumor Activity." J Biol Chem 2005; 280: 19665-19672.
Lu D et al., "Di-diabody: a novel tetravalent bispecific antibody molecule by design." J Immunol Methods 2003; 279: 219-232.
Lu D et al., "Simultaneous Blockade of Both the Epidermal Growth Factor Receptor and the Insulin-like Growth Factor Receptor Signaling Pathways in Cancer Cells with a Fully Human Recombinant Bispecific Antibody." J Biol Chem 2004; 279: 2856-2865.
Mariuzza et al., "The Structural Basis of Antigen-Antibody Recognition." Annu. Rev. Biophys. Biophys. Chem. 1987; 16: 139-159.
Morrison S. "Two heads are better than one " Nature Biotechnology, Nature Publishing Group, New York, NY, US, vol. 25, No. 11, Nov. 1, 2007, pp. 1233-1234.
Refaat Shalaby et al., "Development of Humanized Bispecitic Antibodies Reactive with Cytotoxic Lymphocytes and Tumor Cells Overexpressing the HER2 Protooncogene" J Exp Med 1992; 175:217-225.
Ridgway JB et al., "'Knobs-into-holes' engineering of antibody CH3 domains for heavy chain heterodimerization." (1996) Protein Eng 9: 617-621.
Schaefer et al., "Immunoglobulin domain crossover as a generic approach for the production of bispecific IgG antibodies." PNAS 2011; 108:11187-11192.
Suresh MR et al., "Bispecific Monoclonal Antibodies from Hybrid Hybridomas." Methods Enzymol 1986; 121: 210-228.
Van Der Neut Kolfschoten M et al., "Anti-Inflammatory Activity of Human IgG4 Antibodies by Dynamic Fab Arm Exchange/" Science. 2007 317(5844):1554-7.
Wu C et al., "Simultaneous targeting of multiple disease mediators by a dual-variable-domain immunoglobulin." Nat Biotechnol 2007 25:1290-7.
Zack et al., "Two Kappa Immunoglobulin Light Chains are Secreted by an Anti-DNA Hybridoma: Implications for Isotypic Exclusion." Molecular Immunology, vol. 32(17/18): 1345-1353 (1995).

\* cited by examiner

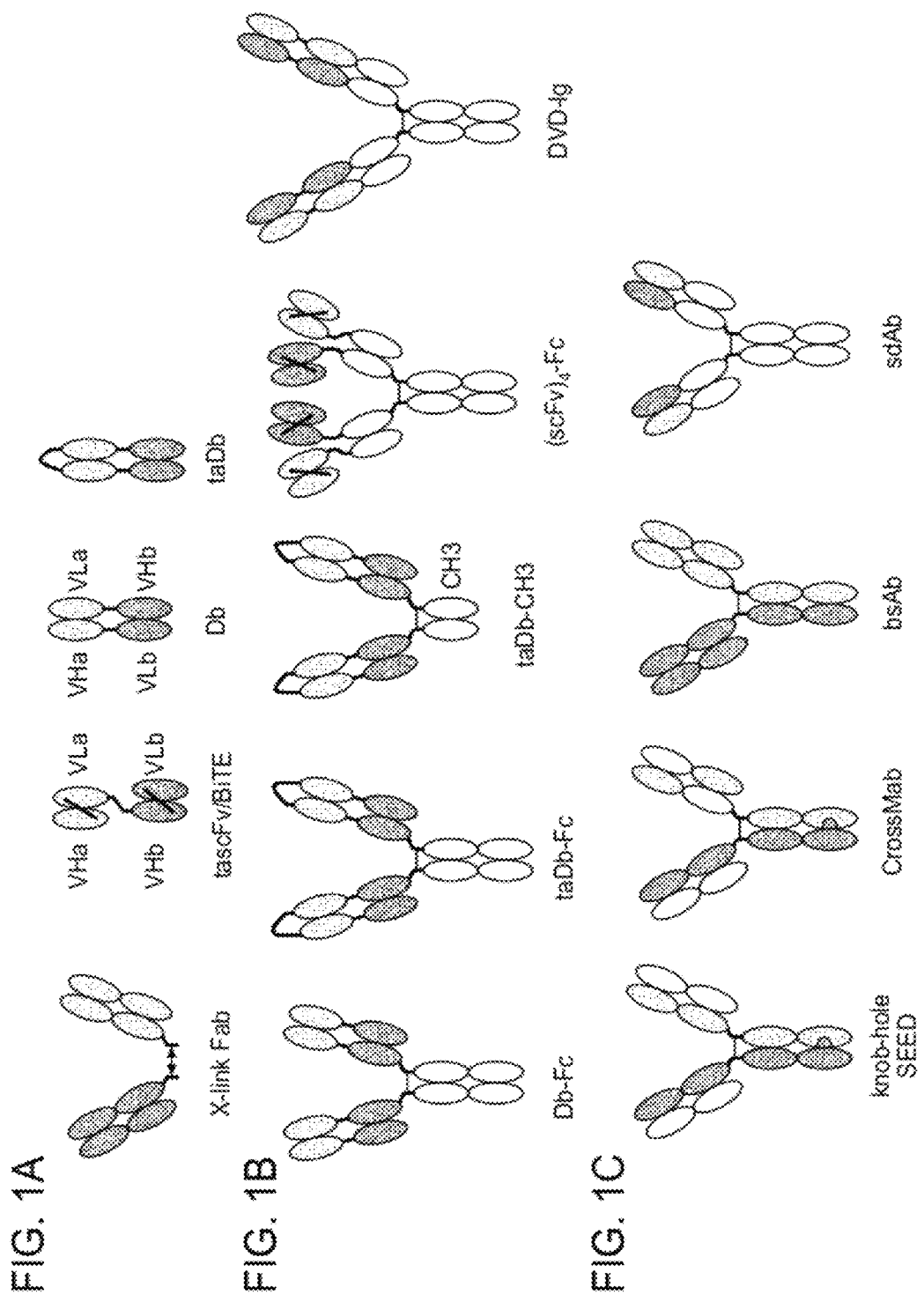

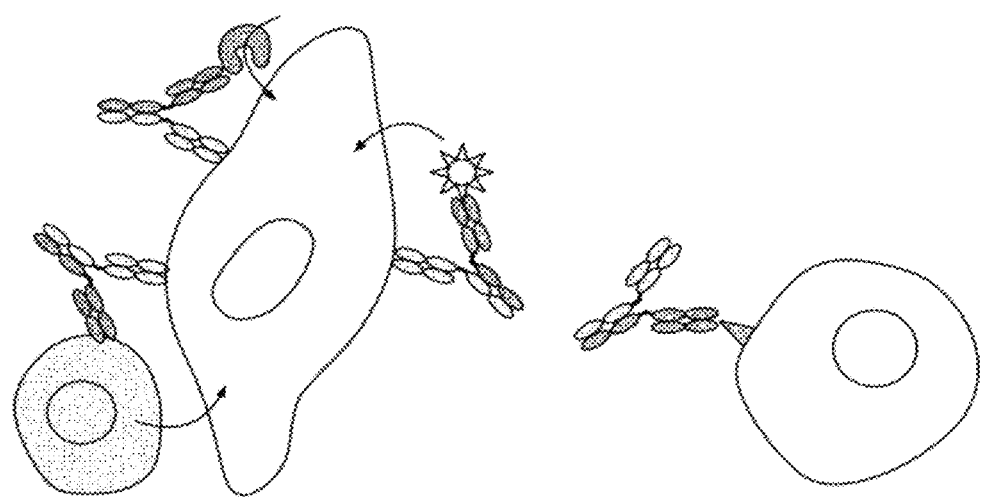
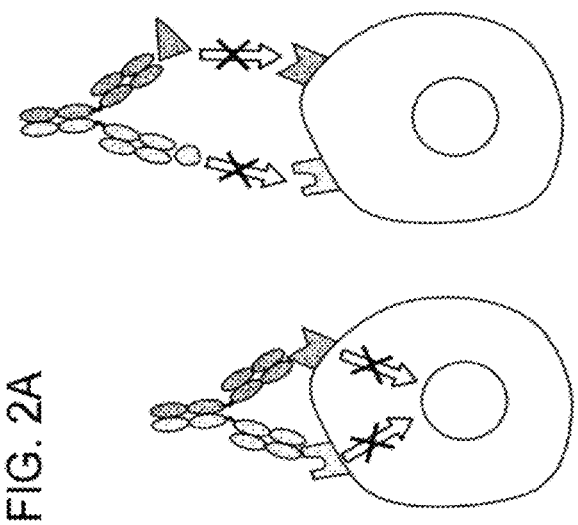
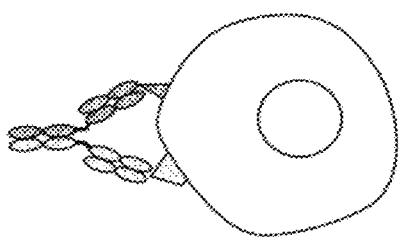
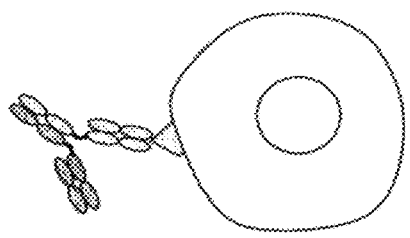
FIG. 2A
FIG. 2B
FIG. 2C

FIG. 5A

VH 3-23 Fixed — AKSYGAFDY — VL λ CDR-L3 Libraries (5 V genes)
VH 3-23 Fixed — AKSYGAFDY — VL κ CDR-L3 Libraries (6 V genes)

FIG. 5B

VH 3-23 Fixed — AKSYGAFDY — VL λ Libraries (all V genes)
VH 3-23 Fixed — AKSYGAFDY — VL κ Libraries (all V genes)

FIG. 5C

VH 3-23 Fixed — ARGDDVS — VL λ CDR-L3 Libraries (5 V genes)
VH 3-23 Fixed — ARGDDVS — VL κ CDR-L3 Libraries (6 V genes)

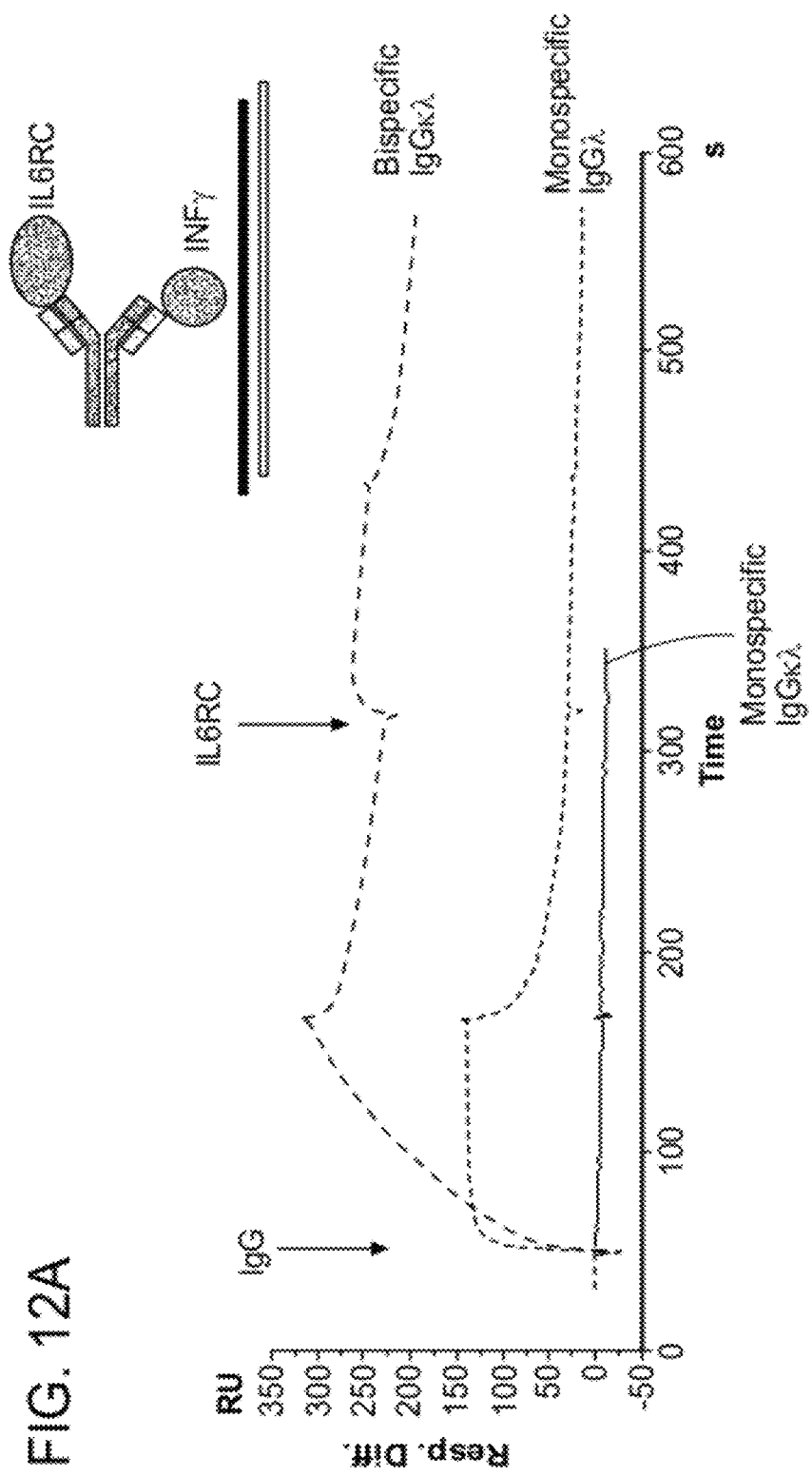

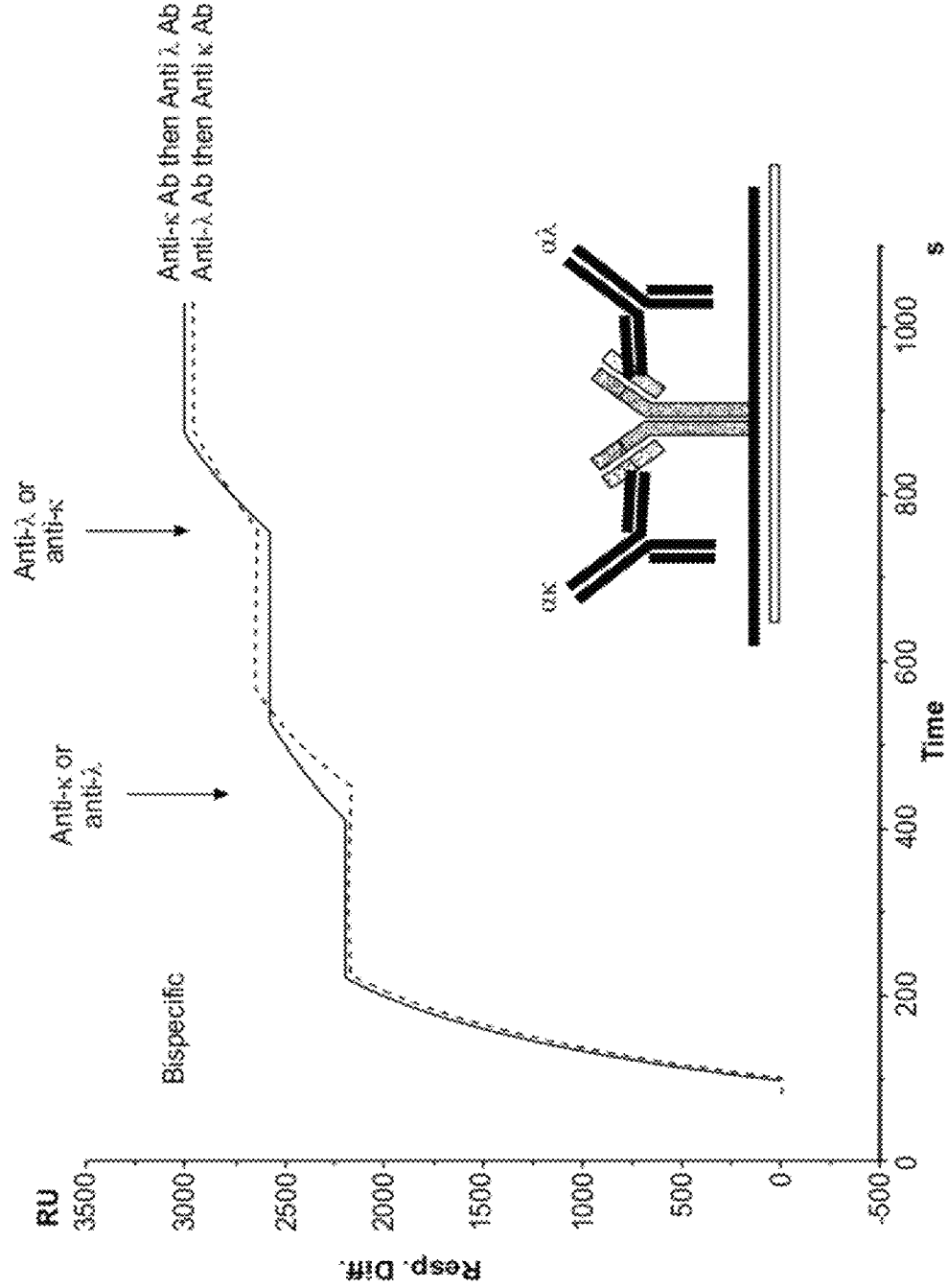

FIG. 17A
FIG. 17B
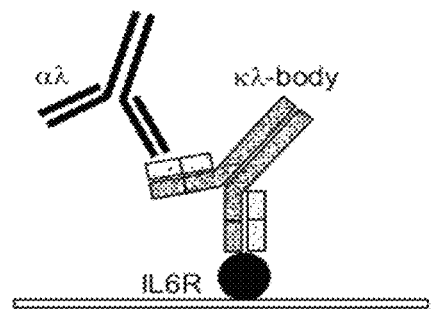
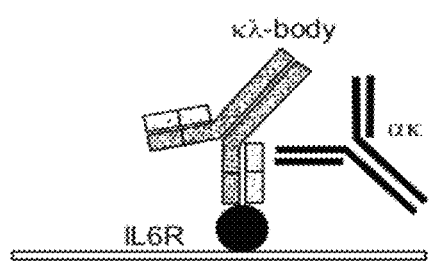
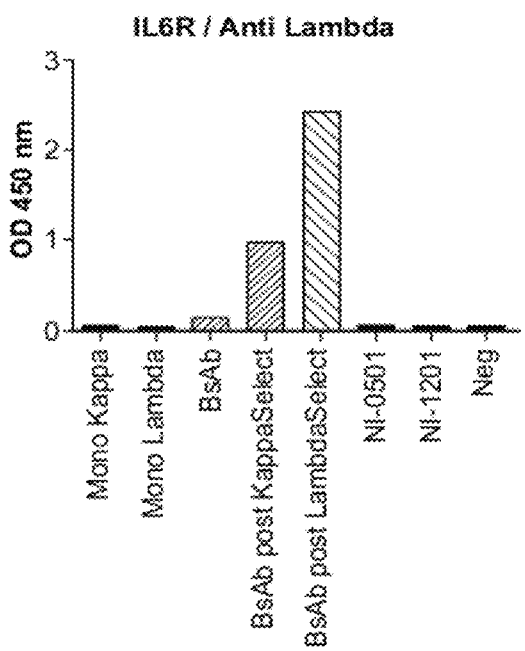
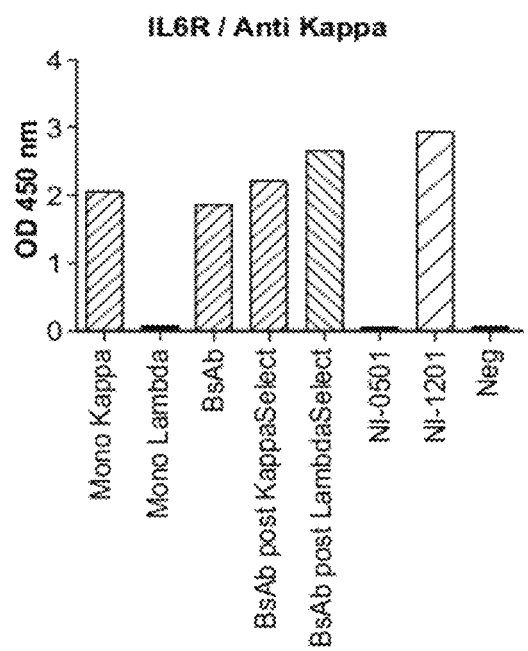

FIG. 17C
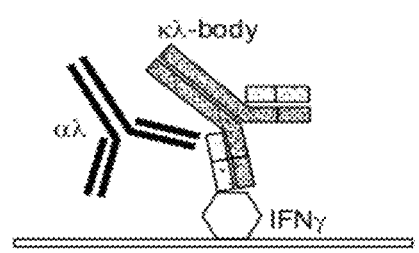
FIG. 17D
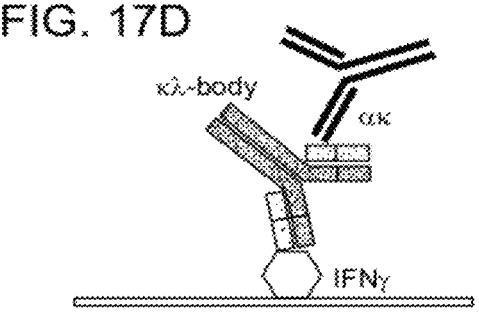
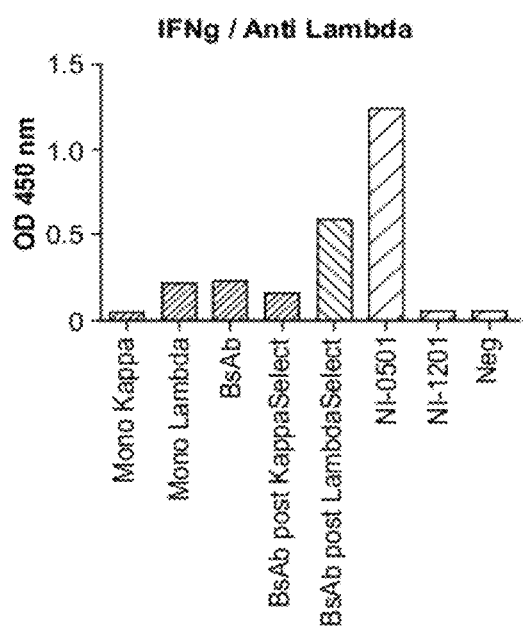
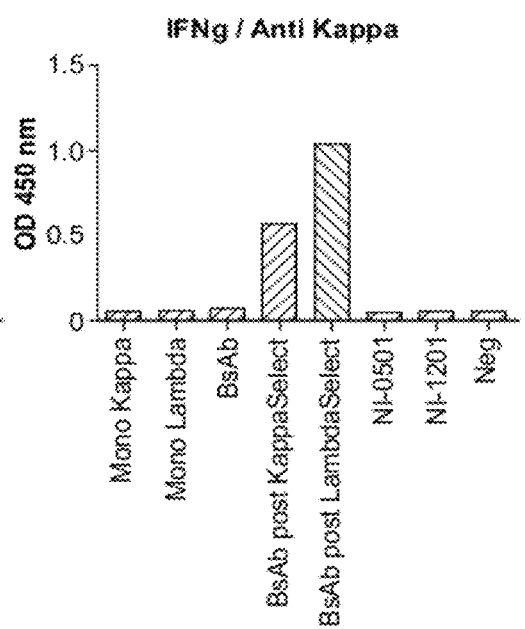

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: chemically synthesized

<400> SEQUENCE: 1

Ala Lys Ser Tyr Gly Ala Phe Asp Tyr
1               5

<210> SEQ ID NO 2
<211> LENGTH: 21
<212> TYPE: DNA
<213> ORGANISM: Artificial Sequence
<220> FEATURE:
<223> OTHER INFORMATION: chemically synthesized

<400> SEQUENCE: 2
ctcttctgag atgagttttt g                                              21

<210> SEQ ID NO 3
<211> LENGTH: 7
<212> TYPE: PRT
<213> ORGANISM: Artificial Sequence
<220> FEATURE:
<223> OTHER INFORMATION: chemically synthesized
```

```
<400> SEQUENCE: 3

Ala Arg Gly Asp Asp Val Ser
1               5

<210> SEQ ID NO 4
<211> LENGTH: 215
<212> TYPE: PRT
<213> ORGANISM: Artificial Sequence
<220> FEATURE:
<223> OTHER INFORMATION: chemically synthesized

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Leu Pro Thr Thr Pro
                85                  90                  95

Ala Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 218
<212> TYPE: PRT
<213> ORGANISM: Artificial Sequence
<220> FEATURE:
<223> OTHER INFORMATION: chemically synthesized

<400> SEQUENCE: 5

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60
```

```
Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Gln Ser Trp
                 85                  90                  95

Asp Gly Asn His Ile Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 6
<211> LENGTH: 445
<212> TYPE: PRT
<213> ORGANISM: Artificial Sequence
<220> FEATURE:
<223> OTHER INFORMATION: chemically synthesized

<400> SEQUENCE: 6

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

-continued

```
Lys Val Asp Lys Arg Val Glu Pro Lys Ser Cys Asp Lys Thr His Thr
    210                 215                 220
Cys Pro Pro Cys Pro Ala Pro Glu Leu Leu Gly Gly Pro Ser Val Phe
225             230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445
```

METHODS FOR THE GENERATION OF MULTISPECIFIC AND MULTIVALENT ANTIBODIES

RELATED APPLICATION

This application claims the benefit of U.S. Provisional Application No. 61/374,159, filed Aug. 16, 2010, U.S. Provisional Application No. 61/443,008, filed Feb. 15, 2011, U.S. Provisional Application No. 61/509,260, filed Jul. 19, 2011, the contents of each of which are hereby incorporated by reference in their entirety.

INCORPORATION OF SEQUENCE LISTING

The contents of the text file named "423001USSeqList.txt", which was created on Mar. 28, 2012 and is 8.67 KB in size, are hereby incorporated by reference in their entirety.

FIELD OF THE INVENTION

The invention relates to the generation of novel bispecific monoclonal antibodies carrying a different specificity for each binding site of the immunoglobulin molecule. The antibodies of the invention are composed of a single heavy chain and two different light chains, one containing a Kappa constant domain and the other of a Lambda constant domain. This invention in particular relates to the isolation of antibodies of different specificities but sharing a common heavy chain. The invention further relates to the controlled co-expression of two light chains and a single heavy chain leading to the assembly of monospecific and bispecific antibodies. The invention provides a mean of producing a fully human bispecific and bivalent antibody that is unaltered in sequence and does not involve the use of linkers or other non-human sequences, as well as antibody mixtures of two monospecific antibodies and one bispecific antibody. The invention also provides the means of efficiently purifying the bispecific antibody.

BACKGROUND OF THE INVENTION

An antibody is composed of four polypeptides: two heavy chains and two light chains. The antigen binding portion of an antibody is formed by the light chain variable domain (VL) and the heavy chain variable domain (VH). At one extremity of these domains six loops form the antigen binding site and also referred to as the complementarity determining regions (CDR). Three CDRs are located on the VH domain (H1, H2 and H3) and the three others are on the VL domain (L1, L2 and L3). During B cell development a unique immunoglobulin region is formed by somatic recombination known as V(D)J recombination. The variable region of the immunoglobulin heavy or light chain is encoded by different gene segments. The heavy chain is encoded by three segments called variable (V), diversity (D) and joining (J) segments whereas the light chain variable is formed by the recombination of only two segments V and J. A large number of antibody paratopes can be generated by recombination between one of the multiple copies of the V, D and J segments that are present in the genome. The V segment encodes the CDR1 and CDR2 whereas the CDR3 is generated by the recombination events. During the course of the immune response further diversity is introduced into the antigen binding site by a process called somatic hypermutation (SHM). During this process point mutations are introduced in the variable genes of the heavy and light chains and in particular into the regions encoding the CDRs. This additional variability allows for the selection and expansion of B cells expressing antibody variants with improved affinity for their cognate antigen.

The vast majority of immunoglobulins are bivalent and monospecific molecules carrying the same specificity on both arms as they are composed of two identical heavy chain polypeptides and two identical light chain polypeptides. However, it was recognized very early during the development of hybridoma technology that hybrid hybridomas can be created by a fusion event between two hybridomas (Suresh M R et al., Methods Enzymol 1986; 121: 210-228). These 'quadromas' express two different heavy and two different light chains and therefore produce a variety of different antibody species resulting from the random pairing of the heavy and light chains. Amongst these different species, bispecific antibodies (bsAbs) are generated, carrying a different specificity on each arm. Another naturally occurring exception is the immunoglobulin of the IgG4 isotype that is able to undergo heavy chain exchange due to a less stable dimerization mediated by the hinge region of that isotype (van der Neut Kolfschoten M et al., Science. 2007 317(5844):1554-7). Although this exchange seems to happen in vivo, its biological significance remains unclear.

Monoclonal antibodies have emerged as a successful and attractive class of molecules for therapeutic intervention in several areas of human disease. However, targeting or neutralizing a single protein is not always sufficient to achieve efficacy in certain diseases which limits the therapeutic use of monoclonal antibodies. It is increasingly clear that in a number of indications neutralizing one component of a biological system is not sufficient to achieve efficacy. One solution to this problem is the co-administration of several monoclonal antibodies. This approach is however complicated by regulatory aspects if the antibodies to be combined have not been previously approved individually. Moreover, combination approaches are also costly from a manufacturing perspective. Accordingly, there exists a need for antibodies and therapeutics that enable targeting of multiple antigens with a single molecule.

SUMMARY OF THE INVENTION

The invention allows for the identification, production and purification of bispecific antibodies that are undistinguishable in sequence from standard antibodies. The invention also allows for the production and purification of a simple antibody mixture of three or more antibodies all bearing the same heavy chain. The unmodified nature of the antibodies of the invention provides them with favorable manufacturing characteristics similar to standard monoclonal antibodies.

The bispecific antibodies of the invention are generated using the following steps:
  Two antibodies having different specificities and sharing the same variable heavy chain domain but different variable light chain domains are isolated. This step is facilitated by the use of antibody libraries having a fixed heavy chain or transgenic animals containing a single VH gene.
  The variable heavy chain domain is fused to the constant region of a heavy chain, one light chain variable domain is fused to a Kappa constant domain and the other variable light chain domain is fused to a Lambda constant domain. Preferably, the light chain variable domain fused to the Kappa constant domain is of the Kappa type and the light chain variable domain fused to the Lambda constant domain is of the Lambda type. However the invention also enables the generation of hybrid light chains so that two variable light chain domains of the same type can be used to generate bispecific antibodies of the invention.

The three chains are co-expressed in mammalian cells leading to the assembly and secretion in the supernatant of a mixture of three antibodies: two monospecific antibodies and one bispecific antibody carrying two different light chains. The ratio of the different antibodies depends on the relative expression of the chains and their assembly into an IgG. The invention provides methods to tune these ratios and maximize the production of bispecific antibody.

The antibody mixture is purified using standard chromatography techniques used for antibody purification. The antibody mixture can be characterized and used as a multi-targeting agent.

The bispecific antibody is purified using in a consecutive manner affinity chromatography media that bind specifically to human Kappa and human Lambda constant regions. This purification process is independent of the sequence of the light chain variable domains and is thus generic for all bispecific antibodies of the invention.

The isolated bispecific antibody bearing a light chain containing a Kappa constant domain and a light chain containing a Lambda constant domain is characterized using different biochemical and immunological methods.

The bispecific antibody of the invention can be used for therapeutic intervention or as a research or diagnostic reagent.

The invention provides monoclonal antibodies carrying a different specificity in each combining site and including two copies of a single heavy chain polypeptide and a first light chain and a second light chain, wherein the first and second light chains are different.

In some antibodies, at least a first portion of the first light chain is of the Kappa type and at least a portion of the second light chain is of the Lambda type. In some antibodies, the first light chain includes at least a Kappa constant region. In some antibodies, the first light chain further includes a Kappa variable region. In some antibodies, the first light chain further includes a Lambda variable region. In some antibodies, the second light chain includes at least a Lambda constant region. In some antibodies, the second light chain further includes a Lambda variable region. In some antibodies, the second light chain further includes a Kappa variable region. In some antibodies, the first light chain includes a Kappa constant region and a Kappa variable region, and the second light chain includes a Lambda constant region and a Lambda variable region.

In some embodiments, the constant and variable framework region sequences are human.

The invention also provides methods to produce and generate a bispecific antibody by a) isolating an antibody or antibody fragment region having a specificity determined by a heavy chain variable domain combined with a first light chain variable domain; b) isolating an antibody or antibody fragment region having a different specificity determined by the same heavy chain variable domain as the antibody of step a) combined with a second light chain variable domain; c) co-expressing in a cell: (i) the common heavy chain variable domain fused to an immunoglobulin heavy chain constant region; (ii) the first light chain variable domain fused either to a light chain constant domain of the Kappa type or fused to a light chain constant domain of the Lambda type; and (iii) the second light chain variable domain fused to a light chain constant domain of a different type than the first variable constant domain.

Some methods also include the additional step of d) isolating the bispecific antibodies produced from the monospecific antibodies produced. For example, in some methods, the isolation is accomplished by using an affinity chromatography purification step. In some methods, the purification step is performed using Kappa constant domain specific, Lambda constant domain or both Kappa constant domain specific and Lambda constant domain specific affinity chromatography media.

In some methods, a Kappa light chain variable domain is fused to a constant region of the Kappa type. In some methods, a Kappa light chain variable domain is fused to a constant region of the Lambda type. In some methods, a Lambda light chain variable domain is fused to a constant region of the Kappa type. In some methods, a Lambda light chain variable domain is fused to a constant region of the Lambda type.

In some methods, step a) and b) are facilitated by the use of antibody libraries having a common heavy chain and diversity confined to the light chain variable domain. The variable heavy chain domain that is foxed in one of such libraries can be based on different variable germline genes and have different sequences both in the CDR and Framework regions. In some methods, such libraries were designed using different types of variable heavy chain domains and could be used to generate antibodies of the invention.

In some methods, the antibody library is displayed on filamentous bacteriophage, at the surface of yeast, bacteria or mammalian cells or used for ribosome or other type of in vitro display.

The invention also provides methods of preparing a bispecific antibody that specifically binds to a first antigen and a second antigen, wherein the first and second antigens are different, by a) providing a first nucleic acid molecule encoding a first polypeptide comprising a heavy variable chain region of an immunoglobulin polypeptide or fragment thereof that binds the first antigen coupled to an immunoglobulin constant region; b) providing a second nucleic acid molecule encoding a second polypeptide comprising a light chain variable region of the immunoglobulin polypeptide or fragment thereof that binds the first antigen coupled to a first Kappa-type or Lambda-type light chain constant region; c) providing a third nucleic acid molecule encoding a third polypeptide comprising a light chain variable region of an immunoglobulin polypeptide or fragment thereof that binds the second antigen coupled to a second Kappa-type or Lambda-type light chain constant region, wherein the first and second light chain constant domains are different types; and d) culturing a host cell comprising the first, second and third nucleic acid molecules under conditions that permit expression of the first, second and third polypeptides.

Some methods also include the further step of e) recovering the bispecific antibody. For example, in some methods, the bispecific antibody is recovered in step e) using an affinity chromatography purification step. In some methods, the purification step is performed using Kappa constant domain specific, Lambda constant domain or both Kappa constant domain specific and Lambda constant domain specific affinity chromatography media.

In some methods, the second nucleic acid encodes a Kappa-type light chain variable domain. In some methods, the second nucleic acid encodes a Kappa-type constant region. In some methods, the second nucleic acid encodes a Lambda-type constant region. In some methods, the second nucleic acid encodes a Lambda-type light chain variable domain. In some methods, the second nucleic acid encodes a Kappa-type constant region. In some methods, the second nucleic acid encodes a Lambda-type constant region. In some methods, the third nucleic acid encodes a Kappa-type light chain variable domain. In some methods, the third nucleic acid encodes a Kappa-type constant region. In some methods, the third nucleic acid encodes a Lambda-type constant region. In some methods, the third nucleic acid encodes a Lambda-type light chain variable domain. In some methods, the third nucleic acid encodes a Kappa-type constant region. In some methods, the third nucleic acid encodes a Lambda-type constant region.

The invention also provides an antibody mixture that includes two monospecific antibodies and one bispecific antibody, all having a common heavy chain. For example, the bispecific antibody is any of the bispecific antibodies described herein or made using methods described herein. The invention also provides methods of generating such an antibody mixture by a) isolating an antibody or antibody fragment region having a specificity determined by a heavy chain variable domain combined with a first light chain variable domain; b) isolating an antibody or antibody fragment region having a different specificity determined by the same heavy chain variable domain as the antibody of step a) combined with a second light chain variable domain; c) co-expressing in a cell: (i) the common heavy chain variable domain fused to an immunoglobulin heavy chain constant region; (ii) the first light chain variable domain fused either to a light chain constant domain of the Kappa type or fused to a light chain constant domain of the Lambda type; and (iii) the second light chain variable domain fused to either to a light chain constant domain of the Kappa type or fused to a light chain constant domain of the Lambda type. Some methods also include the additional step of d) isolating the antibody mixture produced in step c) from cell culture supernatant.

The invention also provides methods for two or more, for example, three or more non-identical antibodies in a single recombinant host cell by a) expressing in the single recombinant host cell one or more nucleic acid sequences encoding a common immunoglobulin heavy chain and at least two, for example, at least three, different immunoglobulin light chains that are capable of pairing with the common immunoglobulin heavy chain to form functional antigen binding domains to produce two or more, for example, three or more, non-identical antibodies that comprise the common heavy chain. Some methods also include the step of harvesting or otherwise purifying the two or more, for example, three or more, non-identical antibodies from the recombinant host cell or from a culture of the host cell. The host cell is, for example, a mammalian cell. In some methods, non-identical antibodies include monospecific and bispecific antibodies.

In some methods, the non-identical antibodies target differing epitopes of the same target antigen. In some methods, the non-identical antibodies have differing affinities for the same target epitope. In some methods, the non-identical antibodies bind to different antigens.

In some methods, the two or more, for example, three or more, non-identical antibodies are independently selected from the group consisting of: IgG1, IgG2, IgG3, IgG4, IgA1, IgA2, IgD, IgE and IgM.

In some methods, the two or more, for example, three or more, non-identical antibodies contain a modified Fc region that modifies the effector functions of the antibodies such as Antigen Dependent Cell mediated Cytotoxicity (ADCC), Complement Dependent Cytotoxiciyt (CDC), Antigen Dependent Cellular Phagocytosis (ADCP) or their pharmacokinetic properties by altering its binding the neonatal Fc Receptors.

In some methods, the two or more, for example three or more different immunoglobulins are in the F(ab')2 format.

In some methods, the one or more nucleic acid sequences are stably expressed in the host cell.

In some methods, the two or more, for example three or more, non-identical antibodies are produced by the host cell in vitro.

Some methods also include the additional steps of selecting at least one host cell by assaying the two or more, for example, three or more, non-identical antibodies produced by the recombinant host cell for their ability to bind a target antigen; culturing the recombinant host cell; and isolating the three or more non-identical antibodies. The antibodies can be isolated using any of the techniques described herein or any other suitable art-recognized method.

In some methods, the different immunoglobulin light chains have identical constant regions. In some methods, the different immunoglobulin light chains have different constant regions.

BRIEF DESCRIPTION OF THE DRAWINGS

FIG. 1 is a schematic representation of different bispecific antibody formats. A. Formats based on antibody fragments: X-Link Fab, cross-linked Fab fragments; tascFv/BiTE, tandem-scFv/Bispecific T cell Engager; Db, diabody; taDb, tandem diabody. B. Formats based on Fc-fusions: Db-Fc, diabody-Fc fusion; taDb-Fc fusion, tandem diabody-Fc fusion; taDb-CH3, tandem diabody-CH3 fusion; (scFv)$_4$-Fc, tetra scFv-Fc fusion; DVD-Ig, dual variable domain immunoglobulin. C. IgG formats: knob-hole and SEED, strand exchange engineered domain; CrossMab, knob-hole combined with heavy and light chain domain exchange; bsAb, quadroma derived bispecific antibody; sdAb, single domain based antibody.

FIG. 2 is a schematic representation of possible modes of action enabled by bispecific antibodies. 2A. Targeting of two antigens. 2B. Retargeting of a toxic moiety or activity to a target cell. 2C. Increase selectivity mediated by avidity.

FIGS. 5A-C are a series illustrations depicting the three types of libraries used in the Examples, for each library type, Vκ and Vλ libraries were kept separated. FIGS. 5A and C: Two sets of libraries that contain a fixed VH3-23 variable domain that differ only by their CDR H3 sequence that is indicated below the H3 (CDR definition according to IMGT). The light chain repertoire was diversified either by inserting randomized sequences into the CDRL3 of selected light chain variable genes (FIGS. 5A and 5C) or by capturing naturally rearranged light chain variable domains isolated from human donors that can include all human variable genes and contain diversity in all 3 CDRs (FIG. 5B). The different diversification strategies are illustrated by horizontal lines below the diversified region of the light chain repertoires.

In FIG. 6A, INFγ was immobilized on the plate, incubated with the anti-INFγ IgGλ or the anti-IL6RC (i.e., IL-6R receptor/IL-6 soluble complex) IgGκ and both were detected with anti-human Cκ or anti-human Cλ antibodies coupled to horse radish peroxidase. The signal was revealed by colorimetry and quantified using a microtiter plate reader.

FIG. 11 depicts the ELISA assays used to determine the capacity of the bispecific antibody to bind both target and the presence of a Kappa and a Lambda light chain in the molecule.

FIG. 12 is an illustration of SPR analysis of IgGκλ bispecific antibodies. In FIG. 12A, INFγ was immobilized at the surface of the Biacore chip and anti-IL6RC monospecific antibody (IgGκ), anti-INFγ monospecific antibody (IgGκ) and, anti-IL6RC/anti-INFγ bispecific antibody (IgGκλ) were injected on the surface followed by injection of IL6RC. In FIG. 12B, the anti-IL6RC/anti-INFγ bispecific antibody (IgGκλ) was immobilized on the chip surface and anti human-Kappa and anti-human Lambda antibodies were injected at the same concentration. The experiment was repeated inverting the order of antibody injection with identical results.

In FIGS. 16A and 16B, the gel was stained using simply blue, and E stands for elution fraction, FT stands for column flow-through and MM stands for molecular weight marker.

FIGS. 17A-D are a series of graphs and illustrations depicting that the methods of generating bispecific antibodies of the invention produce antibodies that include both a Kappa light chain and a Lambda light chain and that the purified antibodies exhibit bispecificity. The graphs depict the results of ELISA using purified κλ-body against hIFNγ and IL6RC. The ELISA was performed using anti-Kappa or anti-Lambda detection antibodies as indicated. FIGS. 17A-D illustrate that the Lambda light chain binds to hIFNγ, while the Kappa light chain binds to IL6RC. NI-0501 is a control anti-hIFNγ Lambda light chain antibody, and NI-1201 is a control anti-IL6RC Kappa light chain antibody.

DETAILED DESCRIPTION

Figure 3A:
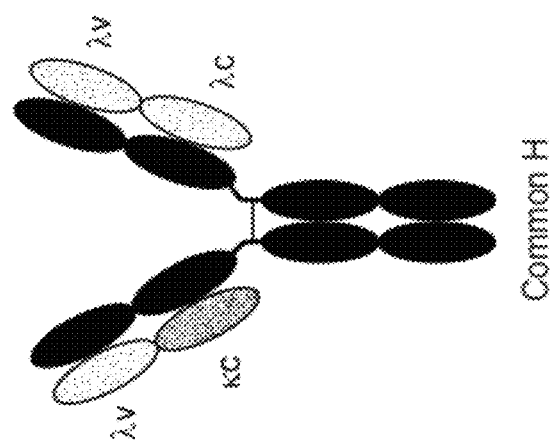
FIGS. 3A-3C are a schematic representation of the structure of different bispecific antibodies of the invention composed of two copies of a unique heavy chain polypeptide and two different light chain polypeptides. The locations and/or arrangements of the Kappa light chain and the Lambda light chain (or portions thereof) shown in these figures are not intended to be limiting. Those of ordinary skill in the art will appreciate that the Kappa light chain and the Lambda light chain (or portions thereof) can also be arranged so as to produce the mirror-image of the bispecific antibodies shown in FIGS. 3A-3C. Those of ordinary skill in the art will also appreciate that the bispecific antibodies that are represented in a full IgG format in FIGS. 3A-3C can also be generated using other immunoglobulin isotypes or in other immunoglobulin formats such as F(ab')2. 3A. Kappa variable domain fused to a Kappa constant domain and Lambda variable domain fused to Lambda constant domain. 3B. Kappa variable domains fused to a Kappa constant domain and a Lambda constant domain. 3C Lambda variable domains fused to a Kappa constant domain and a Lambda constant domain.

In order to overcome the limitations of monoclonal and monovalent antibody therapeutics that can only target a single antigen or to overcome the limitations of combinations of monovalent antibody therapeutics, intense efforts have aimed at multiple antigen targeting using bispecific antibody formats. Such antibodies carrying more than one specificity are of interest in biotechnology and have great potential as therapeutic agents enabling novel therapeutic approaches (Fischer and Leger, Pathobiology 2007; 74:3-14; Morrison SL Nature Biotechnol 2007; 25:1233-1234). Bispecific antibodies are advantageous as they allow for multiple targeting, they increase therapeutic potential, they address redundancy of biological systems, and they provide novel mechanisms of action through abilities such as retargeting and/or increased specificity. As validated single therapeutic targets become more and more exhausted, combinations allowed by bispecific antibodies provide a new and expansive universe of targets for therapeutic agents and applications.

Several strategies have been used to generate such bispecific molecules such as chemical cross-linking of antibody fragments, forced heterodimerization, quadroma technology, fusion of antibody fragments via polypeptide linkers and use of single domain antibodies. The availability of recombinant DNA technologies has lead to the generation of a multitude of bispecific antibody formats (see e.g., Ridgway J B et al. (1996) Protein Eng 9: 617-621). Linkers and mutations have frequently been introduced into different regions of the antibody to force heterodimer formation or to connect different binding moieties into a single molecule. However, these engineered molecules often have poor manufacturing characteristics, as well as an increased risk of immunogenicity, which limit or prevent their progression towards the clinic. In addition, prior attempts to develop bispecific formats have been limited due to factors such as poor stability and/or expression. These approaches are further described below and the formats discussed are illustrated in FIG. 1.

Chemical cross-linking. The use of chemical cross-linking reagents to covalently link two antibodies is a conceptually straightforward approach. Antibody fragments generated from their respective parent antibodies by enzymatic digestion or generated through recombinant technologies are conjugated using bifunctional reagents (Glennie M J et al., J Exp Med 1992; 175:217-225). Product homogeneity is the main limitation of this approach as the bispecific species has to be purified from homodimers and the modification steps can alter the integrity and stability of the proteins. The multiple steps involved make this approach challenging in terms of manufacturing and product homogeneity.

Quadromas. Quadromas and triomas can be generated by fusing either two hybridomas or one hybridoma with a B lymphocyte, respectively (Suresh M R et al., Methods Enzymol 1986; 121: 210-228). In this case the simultaneous expression of two heavy and two light chains leads to the random assembly of 10 antibody combinations and the desired bsAb represent only a small fraction of the secreted antibodies. The bsAb has to be purified using a combination of chromatographic techniques, and dramatically reduces production yields. A major limitation is that quadromas produce bsAb of rodent origin which limit their therapeutic potential due to immunogenicity issues.

Recombinant bispecific antibodies. The majority of bispecific antibody formats have been generated by genetic engineering techniques using antibody fragment such as scFv or Fab fragments as building blocks connected via polypeptide linkers. Formats based on linked antibody fragments include tandem scFv (BiTE), diabodies and tandem-diabodies (Kipriyanov S M. Methods Mol Biol 2003; 207: 323-333; Korn T et al., Int J Cancer 2002; 100:690-697). These building blocks can further be linked to an immunoglobulin Fc region given rise to 'IgG-like' molecules. These formats include diabody-Fc, tandem diabody-Fc, tandem diabody-CH3, (scFv)$_4$-Fc and DVD-Ig (Lu D et al., J Immunol Methods 2003; 279: 219-232; Lu D et al., J Biol Chem 2005; 280: 19665-19672; Lu D et al., J Biol Chem 2004; 279: 2856-2865; Wu C et al., Nat Biotechnol 2007 25:1290-7). A potential limitation of the use of linkers is that the flexible nature of these peptides makes them more prone to proteolytic cleavage, potentially leading to poor antibody stability, aggregation and increased immunogenicity. In addition, these foreign peptides might elicit an immune response against the junction between the protein and the linker or the linker itself. In general bsAbs based on linked building block are challenging molecules in terms of manufacturing which limits their therapeutic potential.

An ideal bispecific molecule for human therapy should be undistinguishable from a normal IgG. Strategies based on forcing the heterodimerization of two heavy chains have been explored. A first approach coined 'knob into hole' aims at forcing the pairing of two different IgG heavy chains by introducing mutations into the CH3 domains to modify the contact interface (Ridgway J B et al., Protein Eng 1996; 9: 617-621). On one chain amino acids with large side chains were introduced, to create a 'knob'. Conversely, bulky amino acids were replaced by amino acids with short side chains to create a 'hole' into the other CH3 domain. By co-expressing these two heavy chains, more than 90% heterodimer formation was observed ('knob-hole') versus homodimers formation ('hole-hole' or 'knob-knob'). A similar concept was developed using strand-exchange engineered domain (SEED) human CH3 domains based on human IgG and human IgA sequences (Davis JH et al., 2010, PEDS 23:195-202). These engineered domains lead to the formation of heterodimeric molecules that can carry two different specificities. These two approaches are attractive as they favor the production of the heterodimer of interest (up to 95%) but do not fully prevent homodimer formation. Therefore downstream purification procedures capable of removing the homodimers from the heterodimers are still required. Another potential issue of these approaches is that the mutated domains are not fully human and can lead to immunogenicity and might also affect the domain stability and aggregation propensity of the molecule. As these strategies allow for the forced paring of the heavy chains, the different light chains can randomly pair with any of the two heavy chains and lead to the generation of different antibodies that need to be purified from one another. Recently an improvement over the 'knob into hole' approach has been described to solve the light chain pairing issue (WO 2009/080253 A1). This method involves the exchange of some of the light chain and heavy chain domains in addition to the 'knob into hole' mutations. The main advantage of this method is that a bispecific bivalent antibody having two different variable heavy chain domains and two different variable light chain domains can be generated and has been coined "CrossMab." However, the sequences of this bispecific antibody are not fully human as it contains both mutations in the Fc to force heterodimerization and non-natural junction points between the different immunoglobulin domains. Furthermore, these modifications lead to reduced expression levels of the bispecific format compared to a standard monoclonal antibody (Schaefer et al., PNAS 2011; 108:11187-11192).

Single domain based antibodies. The immune systems of camelids (lamas and camels) and cartilaginous fish (nurse sharks) use single V-domains fused to a Fc demonstrating that a single domain can confer high affinity binding to an antigen. Camelid, shark and even human V domains represent alternatives to antibodies but they also be used for bsAbs generation. They can be reformatted into a classical IgG in which each arm has the potential to bind two targets either via its VH or VL domain. This single domain-IgG would have biochemical properties similar to an IgG and potentially solve problems encountered with other bsAbs formats in terms of production and heterogeneity. It is however likely that steric hindrance will in often prevent simultaneous binding of both antigens on both antibody arms.

A representation of bispecific antibody formats described above is shown in FIG. 1. Some of these format representations are derived from Fischer and Leger, Pathobiology 2007; 74:3-14; and Morrison SL Nature Biotechnol 2007; 25:1233-1234.

In contrast to these prior formats, the bispecific antibodies, multi-specific antibodies, compositions and methods provided herein overcome such development obstacles. The bispecific antibodies provided herein have a common heavy chain, two light chains—one Kappa (κ), one Lambda (λ)—that each has a different specificity (i.e., two light chains, two specificities). Preferably, the bispecific antibodies do not contain any linkers or other modifications, including amino acid mutations. The methods provided herein produce molecules having specific binding where diversity is restricted to the VL region. These methods produce the bispecific antibodies through controlled co-expression of the three chains (one VH chains, two VL chains), and purification of the bispecific antibody. The bispecific and/or multi-specific antibodies described herein exhibit similar affinities for a given target as compared to the affinities of monospecific antibodies for that same target. Preferably, the bispecific and/or multi-specific antibodies described herein are virtually indistinguishable from standard IgG molecules.

The methods provided herein also provide the means of generating simple antibody mixtures of two monospecific antibodies and one bispecific antibody that are useful, for example, for multiple targeting without purification of the bispecific antibody from the mixture.

Possible Modes of Action of Bispecific Antibodies

Simultaneous inhibition of two targets. By definition bispecific antibodies carry two specificities and can therefore inhibit more than one target. These targets can be soluble factors or located on the surface of a cell. A number formats targeting multiple cytokines have been generated successfully (Wu C et al., Nat Biotechnol 2007 25:1290-7).

Retargeting. As a majority of bispecific antibody formats are capable of binding two molecules simultaneously, they can therefore be used as bridging molecules to retarget cytotoxic effector cells or cytotoxic agents to cells involved in a disease process. This application has been explored in oncology. In some instances, one specificity of an antibody was directed against tumor cell markers such as CD19, CD20, HER2, carcinoembryonic antigen (CEA). The second arm of the bispecific antibody brings in close proximity a toxic moiety or activity such as drugs, toxins, cytokines or an effector cell from the immune system (T cells, NK cells, monocytes and neutrophils, by targeting CD3, CD16, CD64 and CD89, respectively) (Thielemans K, Blood 1996; 87: 4390-4398; Goldstein J et al., J Immunol 1997; 158: 872-879).

Increased specificity via avidity. In a classical IgG format, antibody binding is directed both by the affinity of each combining site for its antigen and on the avidity effects provided by bivalent binding. The avidity effect dramatically increases the apparent affinity of the antibody for cell surface markers as two dissociation events have to occur for the antibody to be released. Some of the bispecific formats described above are bivalent (i.e., one binding site for each target) whereas others are tetravalent. The latter have four binding sites or more and have the potential to bind each target in a bivalent manner. Bivalent bispecific as therapeutic agents selectively targeting cellular populations that express a combination of cell surface markers. This unique mode of action is in principle restricted to molecules that can benefit from an avidity component to discriminate between cells expressing both antigens and those that express only one marker.

A representation of possible modes of action mediated by bispecific antibodies is shown in FIG. 2. This representation is derived from Fischer and Léger, Pathobiology 2007; 74:3-14.

Characteristics and Limitations of Bispecific Antibody Formats

Figure 3B:
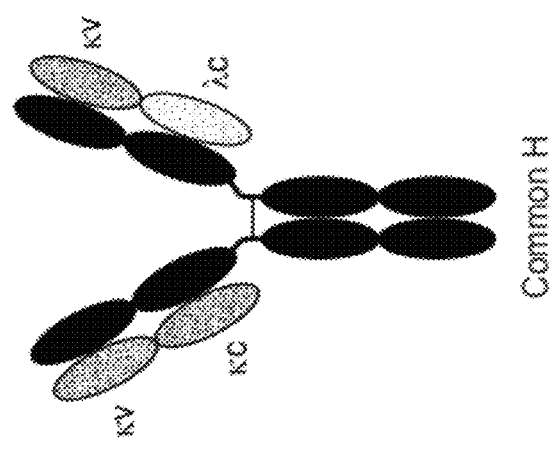
Figure 3C:
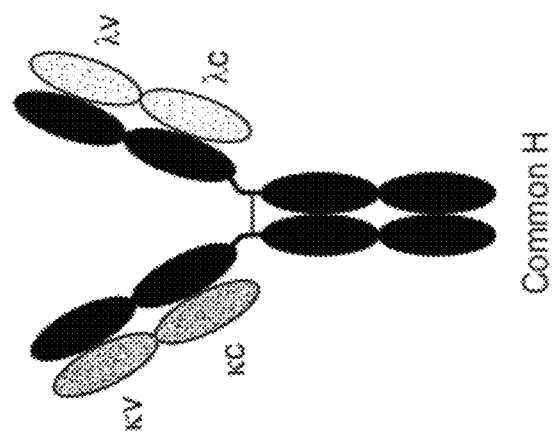

The key characteristics of current bispecific antibody formats are summarized in Table I. All formats except those based on human domains contain sequences that are not of human origin or contain non-human protein sequences generated by the fusion of different protein domains. The majority of formats using linkers lead to potential manufacturing issues due to domain aggregation. The presence of foreign sequences and unfavorable stability characteristics can potentially significantly increase the risk of immunogenicity. A key difference between formats is the valency of their binding sites which is directly linked to their capacity to mediate Retargeting or selective binding mediated by avidity. Thus all formats cannot enable all modes of action. In particular, the only format that is undistinguishable from a fully human immunoglobulin cannot mediate Retargeting or Increased Selectivity activities. There is therefore a need to generate novel bispecific antibodies with favorable properties for the development of therapeutics, i.e., being undistinguishable from a fully human immunoglobulin molecule, good manufacturability properties and enabling the full spectrum of possible modes of actions.

ficity (FIG. 3). The bispecific antibodies described herein are also referred to as IgGκλ antibodies or "κλ bodies," a new fully human bispecific IgG format. This κλ-body format allows the affinity purification of a bispecific antibody that is undistinguishable from a standard IgG molecule with characteristics that are undistinguishable from a standard monoclonal antibody and, therefore, favorable as compared to previous formats.

An essential step of the method is the identification of two antibody Fv regions (each composed by a variable light chain and variable heavy chain domain) having different antigen specificities that share the same heavy chain variable domain. Numerous methods have been described for the generation of monoclonal antibodies and fragments thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies" herein. Human mono-

TABLE I

Characteristics of different bispecific antibody formats.

| | Cross-linked fragments | Quadromas | Recombinant formats - linked antibody fragments | Recombinant formats - forced heterodimers | Recombinant formats - based on single domains |
|---|---|---|---|---|---|
| Binding mode | Bivalent | Bivalent | Tetravalent (or more) | Bivalent | Tetravalent |
| Mode of action | DI, R, IS | DI, R, IS | DI, IS | DI, R, IS | DI |
| Manufacturing | Complex, multistep process | Purification from a complex mixture of antibodies | Can be challenging due to antibody fragment instability and aggregation | Simple mixture (major part of the product is bispecific) | Simple |
| Sequence origin | Human, modified sites by the cross-linking process | Rodent sequences | Human, presence of linkers and non-human protein junctions | Human, presence of mutations to force heterodimerization | Human |

Modes of action:
DI, Dual Inhibition;
R, Retargeting;
IS, Increased Selectivity.

Improved Methods for Generating Bispecific and Bivalent Antibodies.

The present invention provides methods of generating bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions. However it is also possible to obtain bispecific antibodies of the invention by fusing a Kappa light chain variable domain to a constant Lambda domain for a first specificity and fusing a Lambda light chain variable domain to a constant Kappa domain for the second speciclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of techniques are well-known in the art for producing xenogenic non-human animals. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular the CDR3 on the heavy chain is the most diverse CDR in sequence, length and structure. Thus, two antibodies specific for different antigens will almost invariably carry different heavy chain variable domains.

The method of the invention overcomes this limitation and greatly facilitates the isolation of antibodies having the same heavy chain variable domain by the use of antibody libraries in which the heavy chain variable domain is the same for all the library members and thus the diversity is confined to the light chain variable domain. Such libraries are described, for example, in co-pending application PCT/US2010/035619, filed May 20, 2010 and published on Nov. 25, 2010 as PCT Publication No. WO 2010/135558 and co-pending application PCT/US2010/057780, filed Nov. 23, 2010 each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the invention. The bispecific antibodies of the invention can be of different Isotypes and their Fc portion can be modified in order to alter the bind properties to different Fc receptors and in thi sway modifiy the effectors functions of the antibody as well as it pharmacokinetic properties. Numerous methods for the modification of the Fc portion have been described and are applicable to antibodies of the invention. (see for example Strohl, W R Curr Opin Biotechnol 2009 (6):685-91; U.S. Pat. No. 6,528,624; PCT/US2009/0191199 filed Jan. 9, 2009). The methods of the invention can also be used to generate bispecific antibodies and antibody mixtures in a F(ab')2format that lacks the Fc portion.

Another key step of the invention is the optimization of co-expression of the common heavy chain and two different light chains into a single cell to allow for the assembly of a bispecific antibody of the invention. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Therefore the methods of the invention also provide means to modulate the relative expression of the different polypeptides to compensate for their intrinsic expression characteristics or different propensities to assemble with the common heavy chain. This modulation can be achieved via promoter strength, the use of internal ribosome entry sites (IRES) featuring different efficiencies or other types of regulatory elements that can act at transcriptional or translational levels as well as acting on mRNA stability. Different promoters of different strength could include CMV (Immediate-early Cytomegalovirus virus promoter); EF1-1α (Human elongation factor 1α-subunit promoter); Ubc (Human ubiquitin C promoter); SV40 (Simian virus 40 promoter). Different IRES have also been described from mammalian and viral origin. (See e.g., Hellen C U and Sarnow P. Genes Dev 2001 15: 1593-612). These IRES can greatly differ in their length and ribosome recruiting efficiency. Furthermore, it is possible to further tune the activity by introducing multiple copies of an IRES (Stephen et al. 2000 Proc Natl Acad Sci USA 97: 1536-1541). The modulation of the expression can also be achieved by multiple sequential transfections of cells to increase the copy number of individual genes expressing one or the other light chain and thus modify their relative expressions. The Examples provided herein demonstrate that controlling the relative expression of the different chains is critical for maximizing the assembly and overall yield of the bispecific antibody.

The co-expression of the heavy chain and two light chains generates a mixture of three different antibodies into the cell culture supernatant: two monospecific bivalent antibodies and one bispecific bivalent antibody. The latter has to be purified from the mixture to obtain the molecule of interest. The method described herein greatly facilitates this purification procedure by the use of affinity chromatography media that specifically interact with the Kappa or Lambda light chain constant domains such as the CaptureSelect Fab Kappa and CaptureSelect Fab Lambda affinity matrices (BAC BV, Holland). This multi-step affinity chromatography purification approach is efficient and generally applicable to antibodies of the invention. This is in sharp contrast to specific purification methods that have to be developed and optimized for each bispecific antibodies derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

The invention also provides a new means of producing simple antibody mixtures of two or more monospecific antibodies and one or more bispecific antibody that share the same heavy chain and can be purified using standard chromatography techniques used for monoclonal antibody purification. (See e.g., Lowy, I et al. N Engl J Med 2010; 362:197-205; Goudsmit, J. et al. J Infect Dis. 2006. 193, 796-801). Such simple mixtures can be used as multi-targeting agents for therapeutic usage.

Successful co-expression, purification and characterization of the heavy chain and two light chains and purification of the bispecific antibodies are shown in the Examples. The genes encoding the common heavy chain and the two light chains were cloned into a vector containing three promoters. After transient transfection, the supernatant of PEAK cells was collected.

The co-expression of the three chains led to the assembly of three different antibodies: two monospecific and one bispecific antibodies. Their theoretical relative ratios should be 1:1:2 provided the expression levels and assembly rates are similar for both light chains. The bispecific antibodies were purified using a three-step affinity chromatography procedure: (1) Protein A: capture IgG (mono- and bi-), (2) Kappa select: capture IgG containing a Kappa light chain(s), and (3) Lambda select: capture IgG containing a Lambda light chain. Kappaselect and Lambdaselect are affinity chromatography media developed by BAC, BV and GE Healthcare.

Figure 10A:
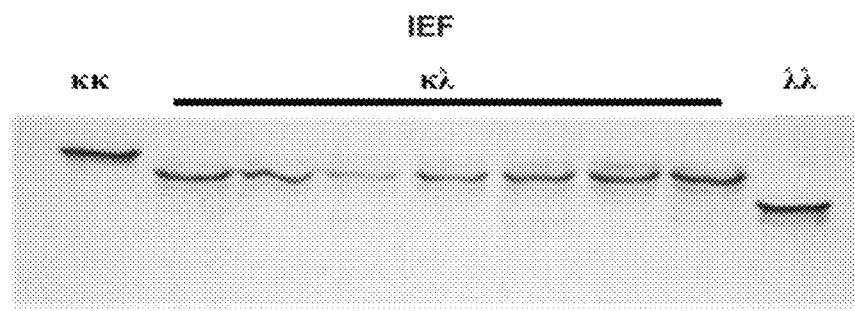
FIG. 10A is an illustration depicting IEF gel analysis of purified monospecific IgG (κκ and λλ) and bispecific IgG (κλ).

The purified bispecific antibodies were characterized as follows. The flow-through and elution from each affinity purification step was analyzed by SDS-PAGE. The results indicate that, at each step, bispecific antibodies are enriched (FIG. 8). The κλ-body contained equivalent amounts of Kappa and Lambda light chains. The κλ-body exhibited an intermediate migration pattern on an isoelectric focusing gel and ion exchange chromatography compared to the two monospecific antibodies (FIG. 10). The specificity and affinity of κλ-bodies was determined by ELISA and surface plasmon resonance. The methods of the invention allow for the identification of antibodies with affinities in the sub-nanomolar to nanomolar range without optimization. This is not obvious as the diversity in antibody libraries described herein is restricted to the light chain which contributes less to the binding energy in standard antibodies.

To avoid the requirement of having access to two antibodies having light chain variable domains of the Kappa and Lambda type being perceived as a limitation to the instant invention, the methods described herein allow for the generation of hybrid light chain in which a Lambda variable domain can be fused to a Kappa constant domain and conversely a Kappa variable domain can be fused to a Lambda constant domain as depicted in FIG. 3. This widens the applications of the invention to antibody pairs that share a light chain of the same type. As described in the Examples provided herein, the fusion point between the variable and constant domains is important and can affect the bispecific antibody purification process.

Figure 13:
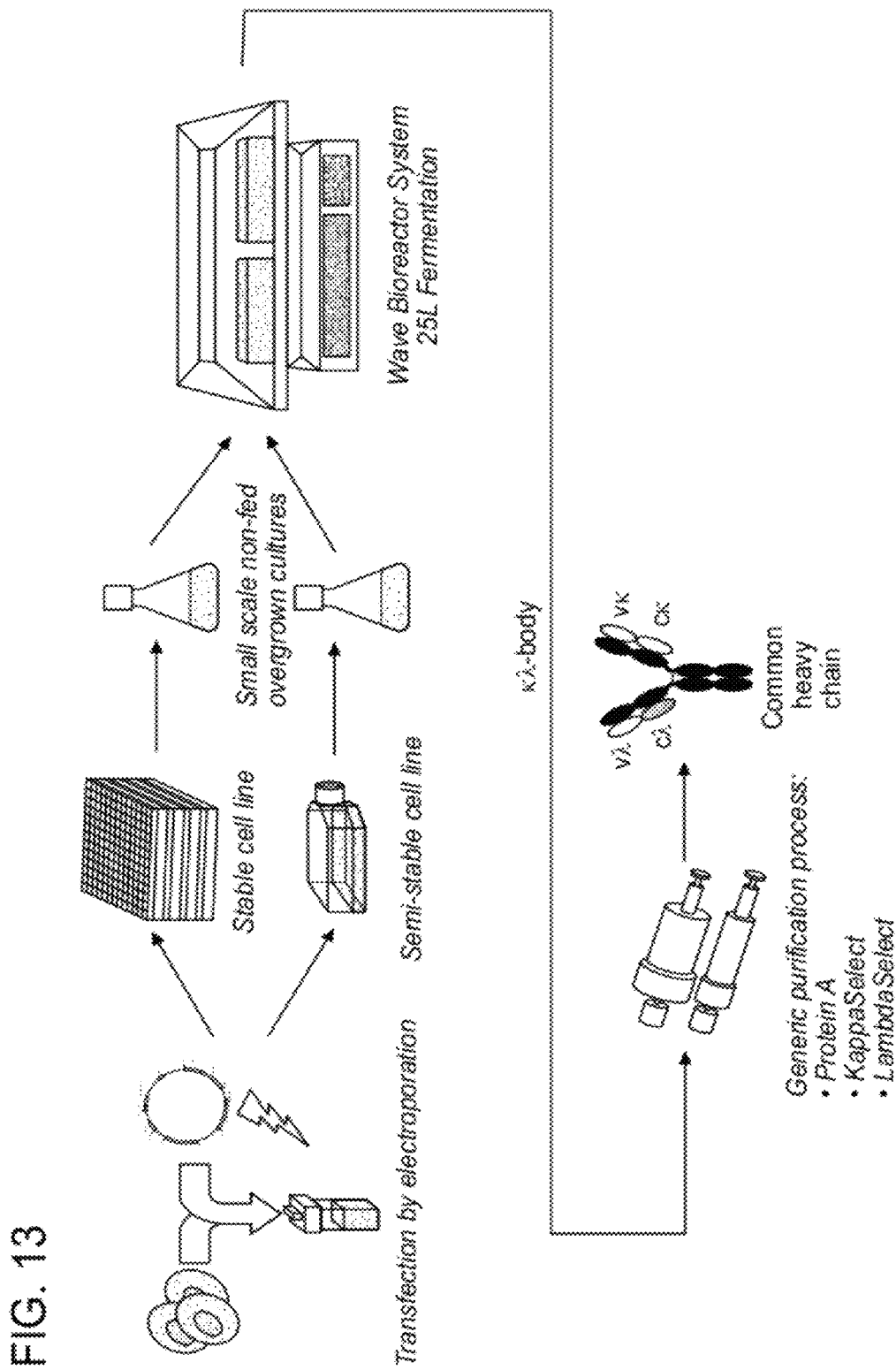
FIG. 13 is a schematic representation of an overview of one method of generating the bispecific and multi-specific antibodies described herein in CHO cells.

An overview of one method of producing the bispecific and/or multi-specific antibodies of the invention is shown in FIG. 13. In some embodiments, the methods of generating bispecific and/or multi-specific antibodies use a complete serum-free chemically defined process. These methods incorporate the most widely used mammalian cell line in pharmaceutical industry, the Chinese Hamster Ovary (CHO) cell line. The methods described therein are used to generate both semi-stable and stable cell lines. The methods can be used to manufacture the bispecific and/or multi-specific antibodies of the invention at small scale (e.g., in an Erlenmeyer flask) and at mid-scale (e.g., in 25 L Wave bag). The methods are also readily adaptable for larger scale production of the bispecific and/or multi-specific antibodies, as well as antibody mixtures of the invention.

Figure 8A:
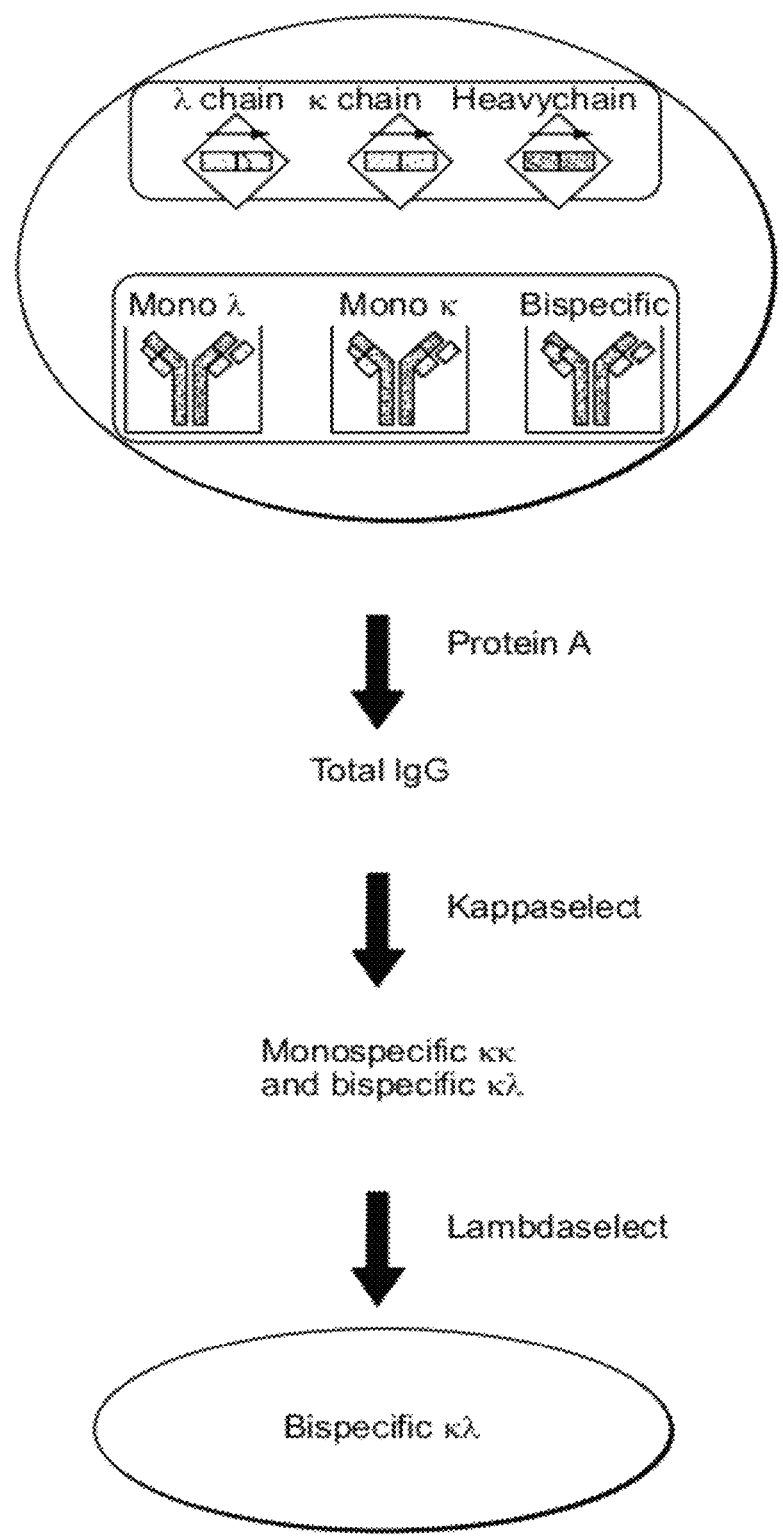
FIG. 8A is a schematic representation of the purification process for bispecific antibodies of the invention.
Figure 16A:
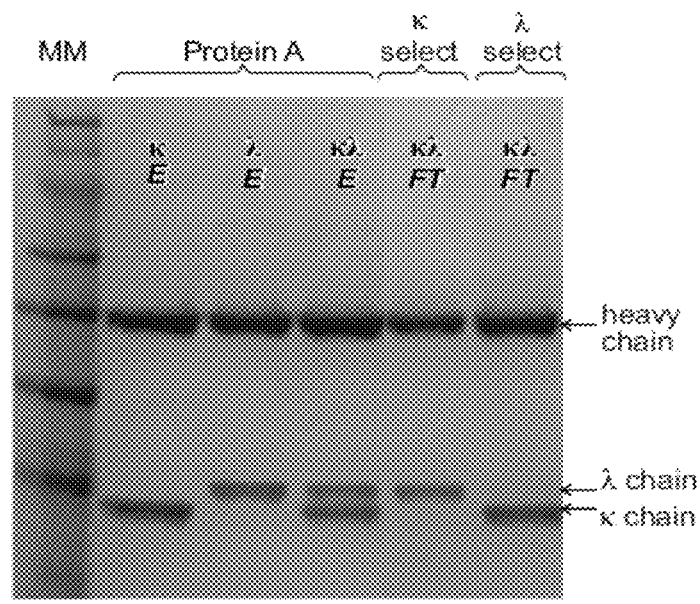
FIG. 16A is an illustration depicting the results of reduced SDS-PAGE analysis of monospecific κ IgG molecules (i.e., monospecific molecules having Kappa light chains, also referred to herein as "mono κ" molecules), monospecific λ IgG molecules (i.e., monospecific molecules having Lambda light chains, also referred to herein as "mono λ" molecules), and κλ antibodies (i.e., antibodies having both Kappa and Lambda light chains) through the purification steps described above.
Figure 16B:
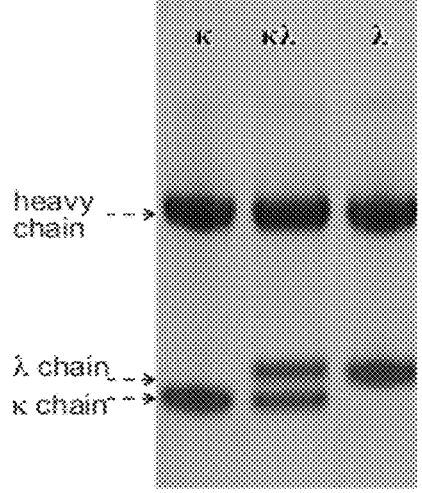
FIG. 16B is an illustration depicting the results of reduced SDS-PAGE analysis of mono κ, mono λ and κλ antibodies obtained following the elution steps described above.
Figure 16C:
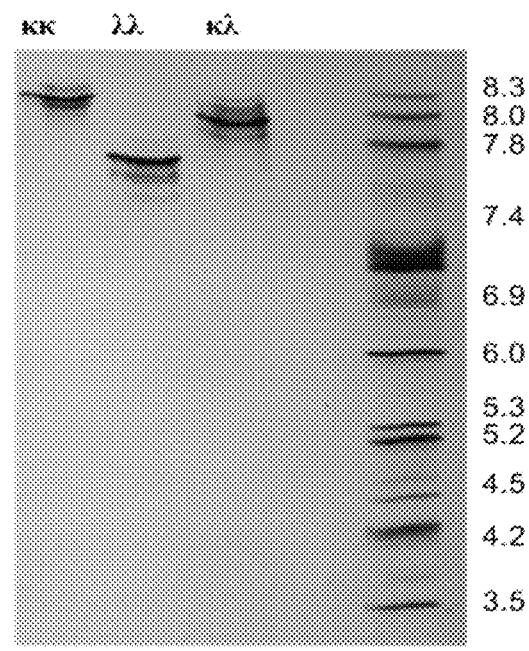
FIG. 16C is an illustration depicting isoelectric focusing (IEF) gel analysis of purified monospecific IgG molecules (κκ and λλ) and the bispecific IgG molecule (κλ).

The methods of generating the bispecific and/or multi-specific antibodies of the invention are advantageous because they employ generic purification processes as shown in FIG. 8A. FIG. 16 demonstrates purification and product integrity testing of bispecific antibodies purified from a semi-stable cell line. The bispecific antibodies were purified using the following three-step affinity chromatography procedure: (i) Protein A purification to capture IgG molecules, including both monospecific and bispecific; (ii) KappaSelect purification to capture IgG containing Kappa light chain(s); (iii) LambdaSelect purification to capture IgG containing Lambda light chain. The flow-through and elution from each affinity purification steps were analyzed by SDS-PAGE. The results demonstrated the removal of each monospecific form (i.e., monospecific IgG molecules having Kappa light chains and monospecific IgG molecules having Lambda light chains) during the purification process (FIG. 16A). The purified κλ-containing antibodies (i.e., antibodies having both Kappa and Lambda light chains) contained equivalent amount of Kappa and Lambda light chains (FIG. 16B). The purified κλ-containing antibodies presented an intermediate migration pattern on an isoelectric focusing gel as compared to the two monospecific antibodies (FIG. 16C).

The chemically defined processes for manufacturing the bispecific and/or multi-specific antibodies of the invention can be used with either pools of CHO cells or with established cell lines. The results obtained with the chemically defined process using either pools or established cell lines demonstrate comparable productivities and growth characteristics to those expressing the corresponding Kappa or Lambda monospecific antibodies. Thus, the κλ-body conserves both the structure and manufacturing characteristics of a classical human IgG.

Previous approaches to produce bispecific antibody formats aimed at forcing the production of a homogenous bispecific molecule using the different antibody engineering approaches described above were done at the expense of productivity, scalability and stability of the product. The present invention is a different approach that allows the production of a simple mixture of antibodies that have the standard characteristics of productivity and scalability of monoclonal antibodies and provides efficient and generic means to purify the bispecific antibody from the mixture or to purify the antibody mixture.

EXAMPLES

Example 1

Generation of Antibody Libraries Having Fixed Heavy Chains

Antibody libraries in which the heavy variable domain is identical for all the library members were generated as follows. First, the heavy chain variable VH3-23 domain containing a defined CDR3AKSYGAFDY (SEQ ID NO: 1) (CDR nomenclature according to IMGT) and a defined FR4 sequence was cloned into the pNDS vector using the SfiI and XhoI restriction sites to obtain the phagemid vector pNDS_VHfixed. The amino acid sequence of Vκ FR4 corresponds to the FR4 region encoded by the germline J genes JK1. The amino acid sequence of Vλ FR4 corresponds to the FR4 region encoded by the germline J genes JL2 and JL3. Two variants of the Vk FR4 sequence were generated with a single amino acid substitution at position 106 (Arginine or Glycine). A total of 6 Kappa (VK1-33, VK1-39, VK3-11, VK3-15, VK3-20, VK4-1) and 5 Lambda variable domain genes (Vλ1-44, Vλ1-51, Vλ6-57, Vλ2-14, Vλ1-40) containing a stuffer fragment instead of a CDR3 encoding sequence were cloned into the pNDS_VHfixed in order to generate 17 acceptor vectors in which diversity of synthetic or natural origin can be cloned and high-diversity libraries can be generated according to the methods described in co-pending application PCT/US2010/035619, filed May 20, 2010, published as WO2010/135558, and the methods described in Ravn et al. (2010) Nucl Acid Res 38(21):e193, each of which is hereby incorporated by reference in its entirety. This process resulted in the generation of 17 libraries all having a common VH3-23 domain and VKappa or VLambda domains diversified in the variable light chain complementarity determining region 3 (CDRL3 region) containing a total of $6.9 \times 10^9$ variants (FIG. 5A). Sequencing of 180 randomly picked transformants indicated that >90% of the clones had integrated a CDRL3 sequence that was in-frame and therefore potentially functional.

Example 2

Phage Rescue of the Libraries

Each library was rescued independently according to standard phage display procedures briefly summarized hereafter. A volume of cells from the frozen library aliquots sufficient to cover at least 10 times the theoretical diversity of the library was added to 500 ml of 2×TYAG (100 μg/ml ampicilin; 2% glucose) and grown at 37° C. with agitation (240 rpm) until an OD600 of 0.3 to 0.5 was reached. The culture was then super-infected with MK13KO7 helper phage and incubated for one hour at 37° C. (150 rpm). The medium was then changed by centrifuging the cells at 2000 rpm for 10 minutes, removing the medium and resuspending the pellet in 500 ml of 2×TY-AK (100 μg/ml ampicilin; 50 μg/ml kanamycin). The culture was then grown overnight at 30° C. (240 rpm). The culture was centrifuged at 4000 rpm for 20 minutes to pellet the cells. The supernatant was collected and 30% (vol/vol) of PEG 8000 (20%)/2.5M NaCl was added to precipitate the phage particles by incubating the mixture 1 hour on ice. The phage particles were collected by centrifugation at 10,000 rpm for 30 minutes and resuspended in 10 ml of TE buffer (10 mM tris-HCl pH 8.0; 1 mM EDTA). The resuspended solution was centrifuged at 10,000 rpm to clear the bacterial debris and the precipitation procedure was repeated. After final resuspension, phage was titrated by infection of *E. coli* and absorption at 260 nm. The display level of scFv at the surface of phage was also evaluated by Western blot analysis using an anti-c-myc monoclonal antibody. Purified phage from different libraries was stored frozen at –80° C. after addition of glycerol to a final concentration of 15% (w/v).

Example 3

Phage Display Selections Using Fixed Heavy Chain Libraries

Liquid phase selections against biotinylated hCXCL10-NusA fusion protein (hCXCL10-NusA) and biotinylated hIL6 receptor complex (hIL6RC): Aliquots of the VH-Vκ and VH-Vλ phage libraries ($10^{11}$-$10^{12}$ Pfu) were kept separated and blocked with PBS containing 3% (w/v) skimmed milk for one hour at room temperature on a rotary mixer. Blocked phage was then deselected on streptavidin magnetic beads (Dynal M-280) for one hour at room temperature on a rotary mixer. Deselected phage was then incubated with in vivo biotinylated hCXCL10-NusA or hIL6RC (100 nM) for two hours at room temperature on a rotary mixer. Beads were added to the target and were captured using a magnetic stand followed by four washes with PBS/0.1% Tween 20 and 3 washes with PBS. Beads were then directly added to 10 ml of exponentially growing TG1 cells and incubated for one hour at 37° C. with slow shaking (100 rpm). An aliquot of the infected TG1 was serial diluted to titer the selection output. The remaining infected TG1 were spun at 3000 rpm for 15 minutes and re-suspended in 0.5 ml 2×TYAG (2×TY media containing 100 μg/ml ampicilin and 2% glucose) and spread on 2×TYAG agar Bioassay plates. After overnight incubation at 30° C., 10 ml of 2×TYAG was added to the plates and the cells were scraped from the surface and transferred to a 50 ml polypropylene tube. 2×TYAG containing 50% glycerol was added to the cell suspension to obtain a final concentration of 17% glycerol. Aliquots of the selection round were kept at –80° C.

Phage rescue: 100 μl of cell suspension obtained from previous selection rounds were added to 20 ml of 2×TYAG and grown at 37° C. with agitation (240 rpm) until an OD600 of 0.3 to 0.5 was reached. The culture was then super-infected with $3.3 \times 10^{10}$ MK13KO7 helper phage and incubated for one hour at 37° C. (150 rpm). The medium was then changed by centrifuging the cells at 3800 rpm for 10 minutes, removing the medium and resuspending the pellet in 20 ml of 2×TY-AK (100 μg/ml ampicilin; 50 μg/ml kanamycin). The culture was then grown overnight at 30° C. (240 rpm). The next day an aliquot of the centrifuged supernatant was used as an input for the next round of selection.

Monoclonal phage rescue for ELISA: Single clones were picked into a microtiter plate containing 150 μl of 2×TYAG media (2% glucose) per well and grown at 37° C. (100-120 rpm) for 5-6 h. M13KO7 helper phage was added to each well to obtain a multiplicity of infection (MOI) of 10 (i.e., 10 phage for each cell in the culture) and incubated at 37° C. (100 rpm) for 1 h. Following growth, plates were centrifuged at 3,200 rpm for 10 min. Supernatant was carefully removed, cells resuspended in 150 μl 2×TYAK medium and grown overnight at 30° C. (120 rpm). For the ELISA, the phage are blocked by adding 150 μl of 2× concentration PBS containing 5% skimmed milk powder followed by one hour incubation at room temperature. The plates were then centrifuged 10 minutes at 3000 rpm and the phage containing supernatant used for the ELISA.

Figure 4:
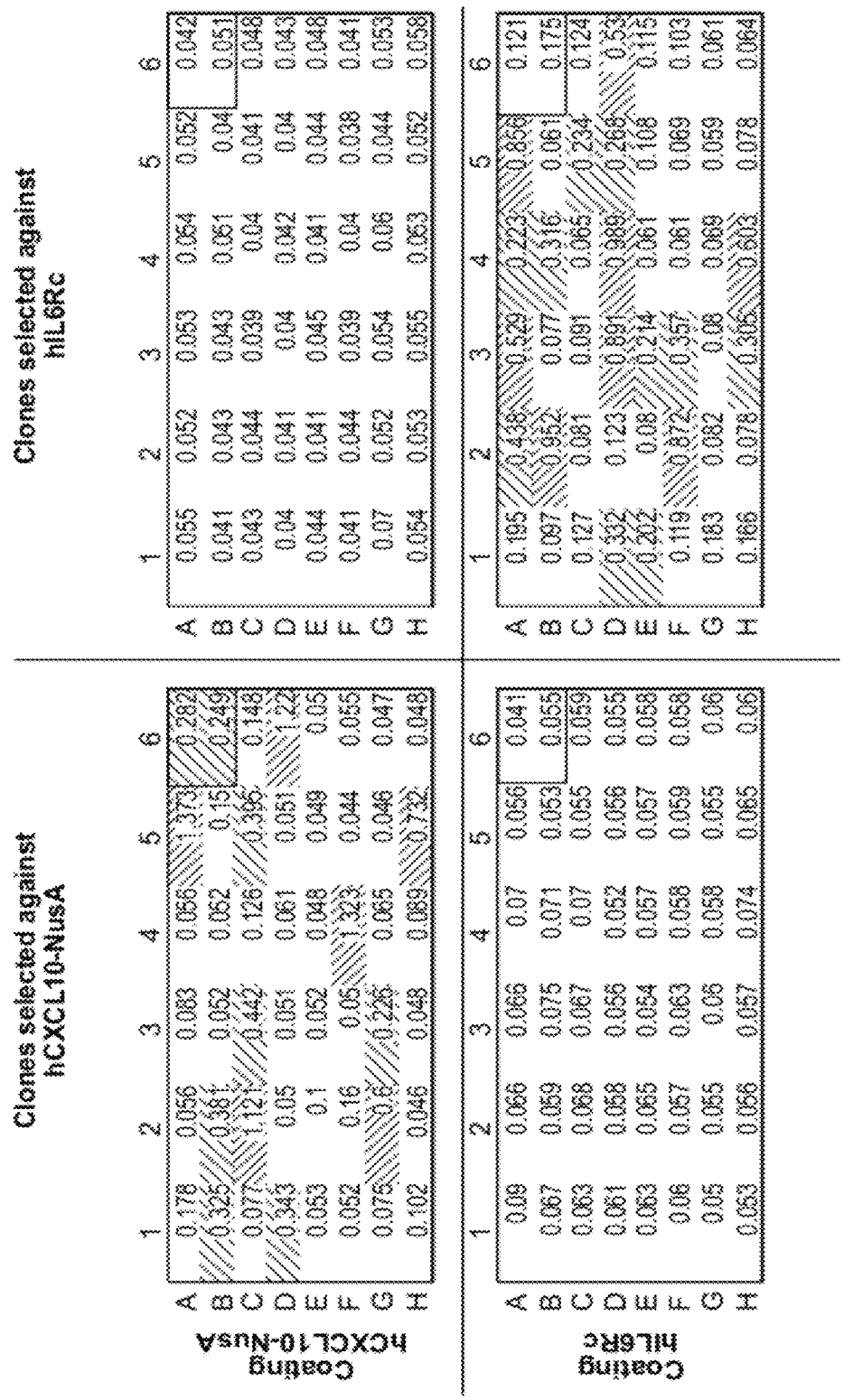
FIG. 4 is an illustration of an ELISA assay testing clones specific for hCXCL10-NusA or hIL6C and bearing the same variable heavy chain domain. Each clone was tested against both targets to demonstrate specificity.

Phage ELISA: ELISA plates (Maxisorp, NUNC) were coated overnight with 2 μg/ml hCXCL10-NusA in PBS or 2 μg/ml hIL6RC in PBS. Plates were then blocked with 3% skimmed milk/PBS at room temperature for 1 h. Plates were washed 3 times with PBS 0.05% Tween 20 before transferring the pre-blocked phage supernatants and incubation for one hour at room temperature. Each clone was tested against both targets to test its specificity. Plates were then washed 3 times with PBS 0.05% Tween 20. 50 μl of 3% skimmed milk/PBS containing (HRP)-conjugated anti-M13 antibody (Amersham, diluted 1:10,000) to each well. Following incubation at room temperature for 1 hr, the plates were washed 5 times with PBS 0.05% Tween 20. The ELISA was then revealed by adding 50 μl of TMB (Sigma) and 50 μl of 2N $H_2SO_4$ to stop the reaction. Absorption intensity was read at 450 nm. Clones specific for hCXCL10-NusA or hIL6RC bearing the same variable heavy chain domain could be identified. (FIG. 4).

Phage clone sequencing: Single clones were grown in 5 ml of 2×TYAG media (2% glucose) per well and grown at 37° C. (120 rpm) overnight. The next day phagemid DNA was purified and used for DNA sequencing using a primer specific for pNDS1: mycseq, 5'-CTCTTCTGAGAT-GAGTTTTTG. (SEQ ID NO: 1).

Large scale scFv purification: A starter culture of 1 ml of 2×TYAG was inoculated with a single colony from a freshly streaked 2×TYAG agar plate and incubated with shaking (240 rpm) at 37° C. for 5 hours. 0.9 ml of this culture was used to inoculate a 400 ml culture of the same media and was grown overnight at 30° C. with vigorous shaking (300 rpm). The next day the culture was induced by adding 400 µl of 1M IPTG and incubation was continued for an additional 3 hours. The cells were collected by centrifugation at 5,000 rpm for 10 minutes at 4° C. Pelleted cells were resuspended in 10 ml of ice-cold TES buffer complemented with protease inhibitors as described above. Osmotic shock was achieved by adding 15 ml of 1:5 diluted TES buffer and incubation for 1 hour on ice. Cells were centrifuged at 10,000 rpm for 20 minutes at 4° C. to pellet cell debris. The supernatant was carefully transferred to a fresh tube. Imidazole was added to the supernatant to a final concentration of 10 mM. 1 ml of Ni-NTA resin (Qiagen), equilibrated in PBS was added to each tube and incubated on a rotary mixer at 4° C. (20 rpm) for 1 hour. The tubes were centrifuged at 2,000 rpm for 5 minutes and the supernatant carefully removed. The pelleted resin was resuspended in 10 ml of cold (4° C.) Wash buffer 1 (50 mM $NaH_2PO_4$, 300 mM NaCl, 10 mM imidazole, pH to 8.0). The suspension was added to a polyprep column (Biorad). 8 ml of cold Wash Buffer 2 (50 mM $NaH_2PO_4$, 300 mM NaCl, 20 mM imidazole, pH to 8.0) were used to wash the column by gravity flow. The scFv were eluted from the column with 2 ml of Elution buffer (50 mM $NaH_2PO_4$, 300 mM NaCl, 250 mM imidazole, pH to 8.0). Fractions were analyzed by absorption at 280 nm and protein containing fractions were pooled before buffer exchange on a NAP5 desalting column (Amersham) equilibrated with PBS. The scFv in PBS were analyzed by SDS-PAGE and quantified by absorption at 280 nm. The purified scFv were aliquoted and stored at −20° C. and at 4° C. The purified scFv were used in ELISA to confirm specific binding to the target against which they had been selected.

Example 4

Additional Selections using Different Fixed VH Libraries

Antibody libraries were also generated by capturing naturally rearranged light chain repertoires and cloning them in the context of a single VH domain described in Example 1. In this case the whole light chain variable gene region was amplified from human cDNA using primers that correspond to the 5' and 3' region of human rearranged variables regions and cloned into pNDS_VHfixed vector described in Example 1. Another set of libraries was generated as described in Example 1 but using a fixed VH3-23 domain containing a different CDRH3 sequence ARGDDVS (SEQ ID NO:3). The libraries described above are schematically represented in FIG. 5. These fixed VH libraries were used against a panel of target proteins using the selection and screening methodology described in Example 2 and 3. Selections have been performed using the following targets: hCXCL10-NusA, IL-6RC, CD47, CD16, CD8 and hIFNγ. Candidates that were identified and shown to be specific for their targets are listed in Table II. These results demonstrate that antibodies binding different targets and having a common heavy chain can be generated and that diversity restricted to the light chain is sufficient to confer antigen specificity. Candidates could be generated from libraries containing a VH3-23 domain with different CDRH3 sequences or having VL repertoires diversified using different strategies. Therefore, the results demonstrate that the approach is not restricted to a particular VH sequence or to a particular light chain variable domain diversification strategy.

TABLE II

Number of independent clones identified against a panel of targets using libraries with a fixed VH sequence containing two different CDRH3 sequences.

| | Total | | Fixed CDRH3 SEQ ID: 1 | | Fixed CDRH3 SEQ ID: 3 | |
|---|---|---|---|---|---|---|
| Targets: | κ | λ | κ | λ | κ | λ |
| hCD16 | 5 | 1 | 4 | — | — | 1 |
| hCD8 | 5 | 12 | 2 | 10 | 3 | 2 |
| hCD47 | 21 | 9 | 16 | 4 | 5 | 5 |
| IL6RC | 17 | 14 | 8 | 7 | 9 | 7 |
| IFNγ | — | 5 | — | 5 | — | — |
| NusA-CXCL10 | 2 | 4 | 2 | 4 | NA | NA |

NA: selection not performed.

Example 5

Figure 6A:
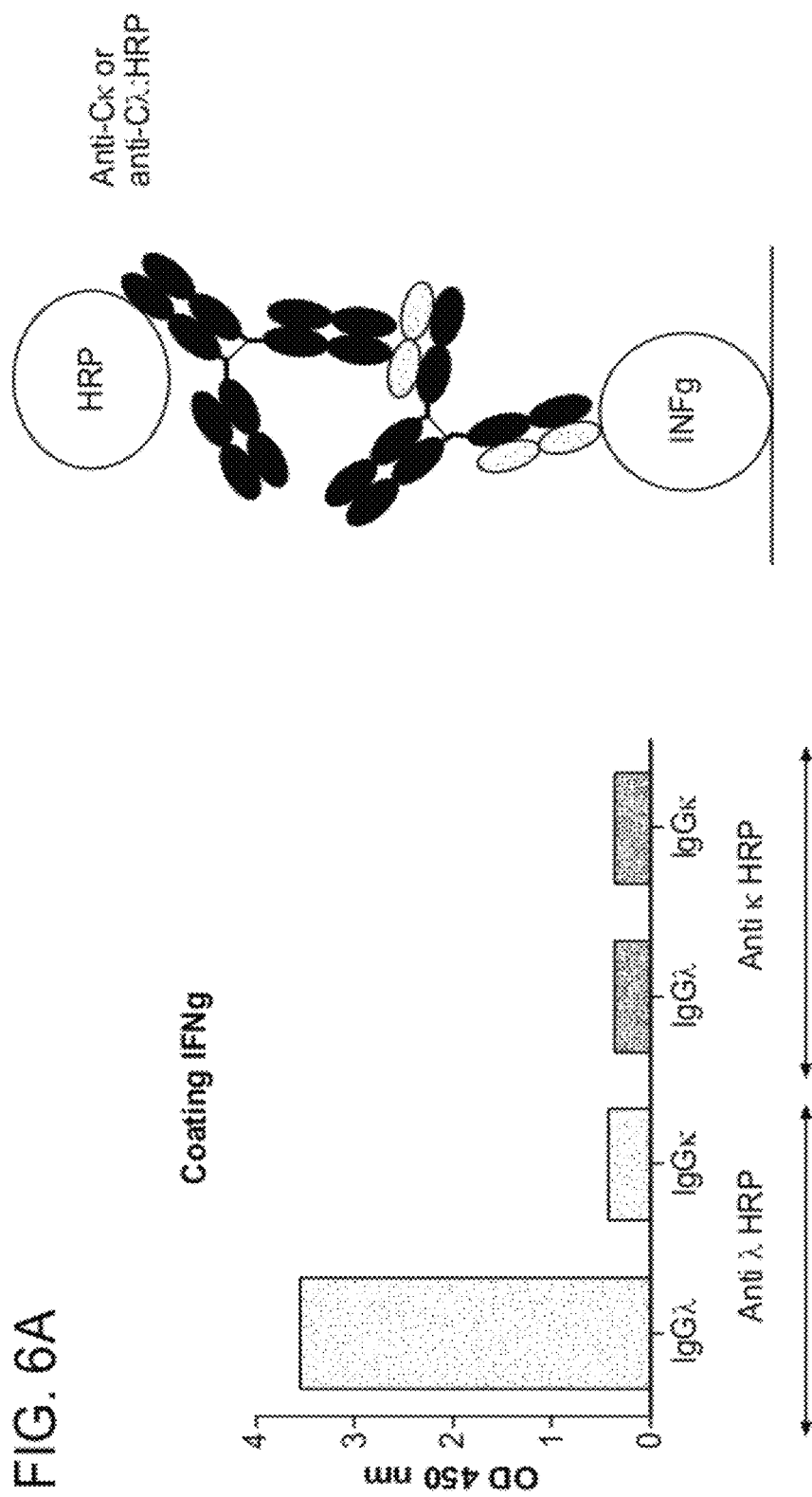
FIGS. 6A-6B are graphs depicting the results of ELISA using monospecific IgGλ and IgGκ selected against hIFNγ and IL6RC, respectively and bearing a common heavy chain. The ELISA formats are schematically represented next to each graph.
Figure 6B:
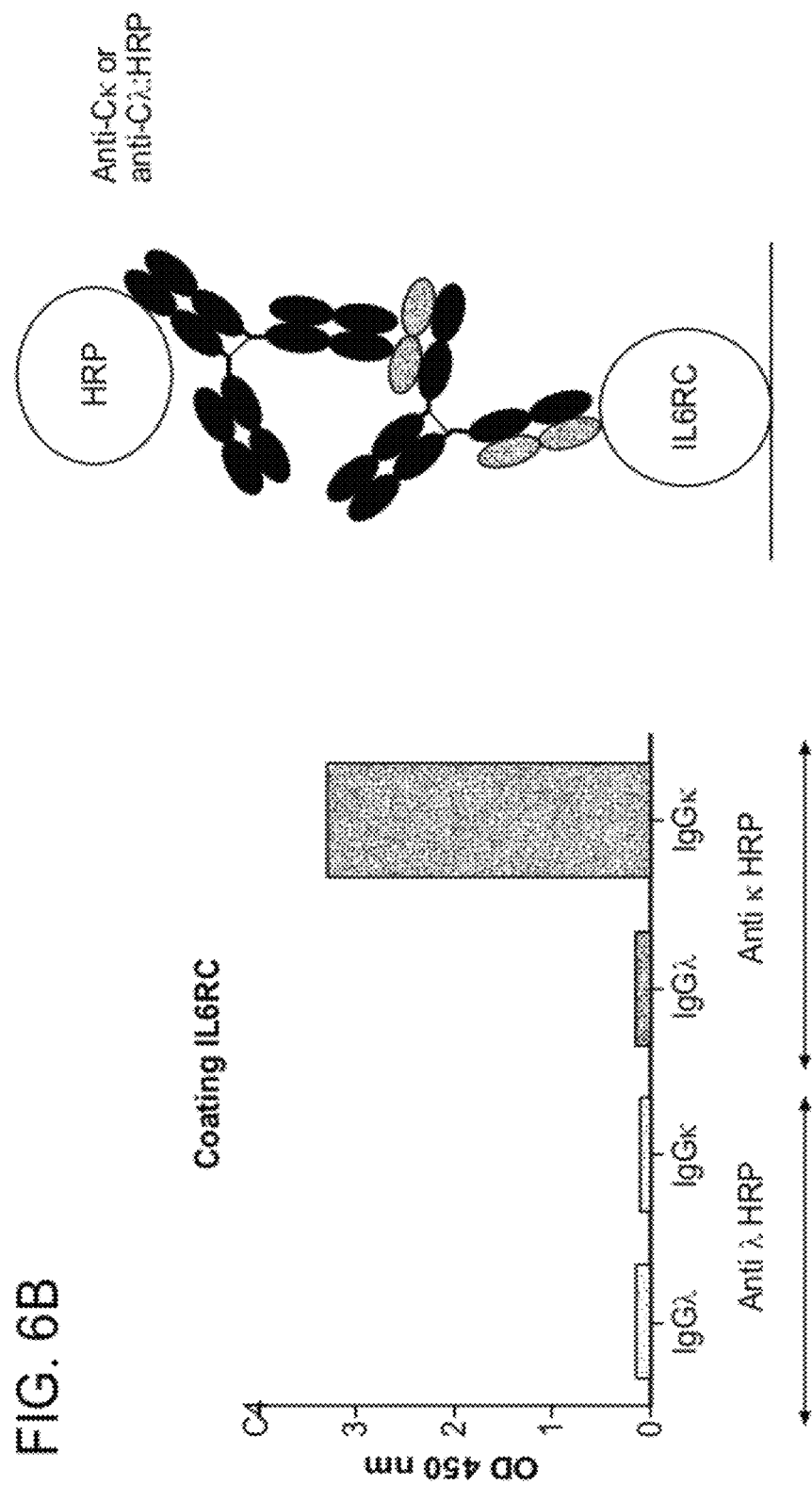

Fixed VH Candidates Reformatting into IgG and Transient Expression in Mammalian Cells After screening, scFv candidates were reformatted into IgG and expressed by transient transfection into PEAK cells. Several IgGλ (n=5) and IgGκ (n=9) having a common heavy chain and specific for IFNγ and IL6RC, respectively, and having different light chain sequences were generated as follow. The VH and VL sequences of selected scFv were amplified with specific oligonucleotides and cloned into an expression vector containing the heavy and light chain constant regions and the constructions were verified by sequencing. The expression vectors were transfected into mammalian cells using the Fugene 6 Transfection Reagent (Roche, Basel, Switzerland). Briefly, Peak cells were cultured in 6-well plates at a concentration of $6 \times 10^5$ cells per well in 2 ml culture media containing fetal bovine serum. The expression vectors encoding the candidate VH and VL sequences were co-transfected into the cells using the Fugene 6 Transfection Reagent according to manufacturer's instructions. One day following transfection, the culture media was aspirated, and 3 ml of fresh serum-free media was added to cells and cultured for three days at 37° C. Following three days culture period, the supernatant was harvested for IgG purified on protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE. The IgG were then tested for binding by to IFNγ and the IL-6/IL-6R receptor complex, referred to herein as IL6RC, by ELISA. Biotinylated IFNγ and IL6RC were immobilized on streptavidin coated microplates (Streptawell, Roche) and the plates were then blocked with PBS supplemented with 2% BSA at room temperature for 1 h. Plates were washed 3 times with PBS 0.05% Tween 20 before adding the purified anti-INFγ IgGλ or the anti-IL6RC IgGκ on wells coated with either target. After one hour incubation at room temperature and washing of the plates bound antibodies were detected with anti-human Cκ or anti-human Cλ antibodies coupled to horse radish peroxidase. The ELISA was then revealed by adding 50 μl of TMB (Sigma) and 50 μl of 2N $H_2SO_4$ to stop the reaction. Absorption intensity was read at 450 nm. The results indicate that the binding specificity of the scFv isolated from the fixed VH libraries was maintained in the IgG format and demonstrated that two IgGs having the same heavy chain but different light chains can be specific for distinct targets (FIG. 6).

The heavy and light chain amino acid sequences of the anti-INFγ IgGλ or the anti-IL6RC IgGκ are indicated below:

```
Anti-IL6RC VKappa light chain
                                                    (SEQ ID NO: 4)
EIVLTQSPATLSLSPGERATLSCRASQSVSSYLAWYQQKPGQAPRLLIYDASNRATGIPARFSG

SGSGTDFTLTISSLEPEDFAVYYCQQWLPTTPATFGQGTKVEIKRTVAAPSVFIFPPSDEQLKS

GTASVVCLLNNFYPREAKVQWKVDNALQSGNSQESVTEQDSKDSTYSLSSTLTLSKADYEKHKV

YACEVTHQGLSSPVTKSFNRGEC

Anti-INFγ VLambda light chain
                                                    (SEQ ID NO: 5)
NFMLTQPHSVSESPGKTVTISCTRSSGSIASNYVQWYQQRPGSSPTTVIYEDNQRPSGVPDRFS

GSIDSSSNSASLTISGLKTEDEADYYCQSQSWDGNHIVFGGGTKLTVLGQPKAAPSVTLFPPSS

EELQANKATLVCLISDFYPGAVTVAWKADSSPVKAGVETTTPSKQSNNKYAASSYLSLTPEQWK

SHRSYSCQVTHEGSTVEKTVAPTECS

Common heavy chain
                                                    (SEQ ID NO: 6)
EVQLLESGGGLVQPGGSLRLSCAASGFTFSSYAMSWVRQAPGKGLEWVSAISGSGGSTYYADSV

KGRFTISRDNSKNTLYLQMNSLRAEDTAVYYCAKSYGAFDYWGQGTLVTVSSASTKGPSVFPLA

PSSKSTSGGTAALGCLVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPG.
```

Example 6

Figure 7A:
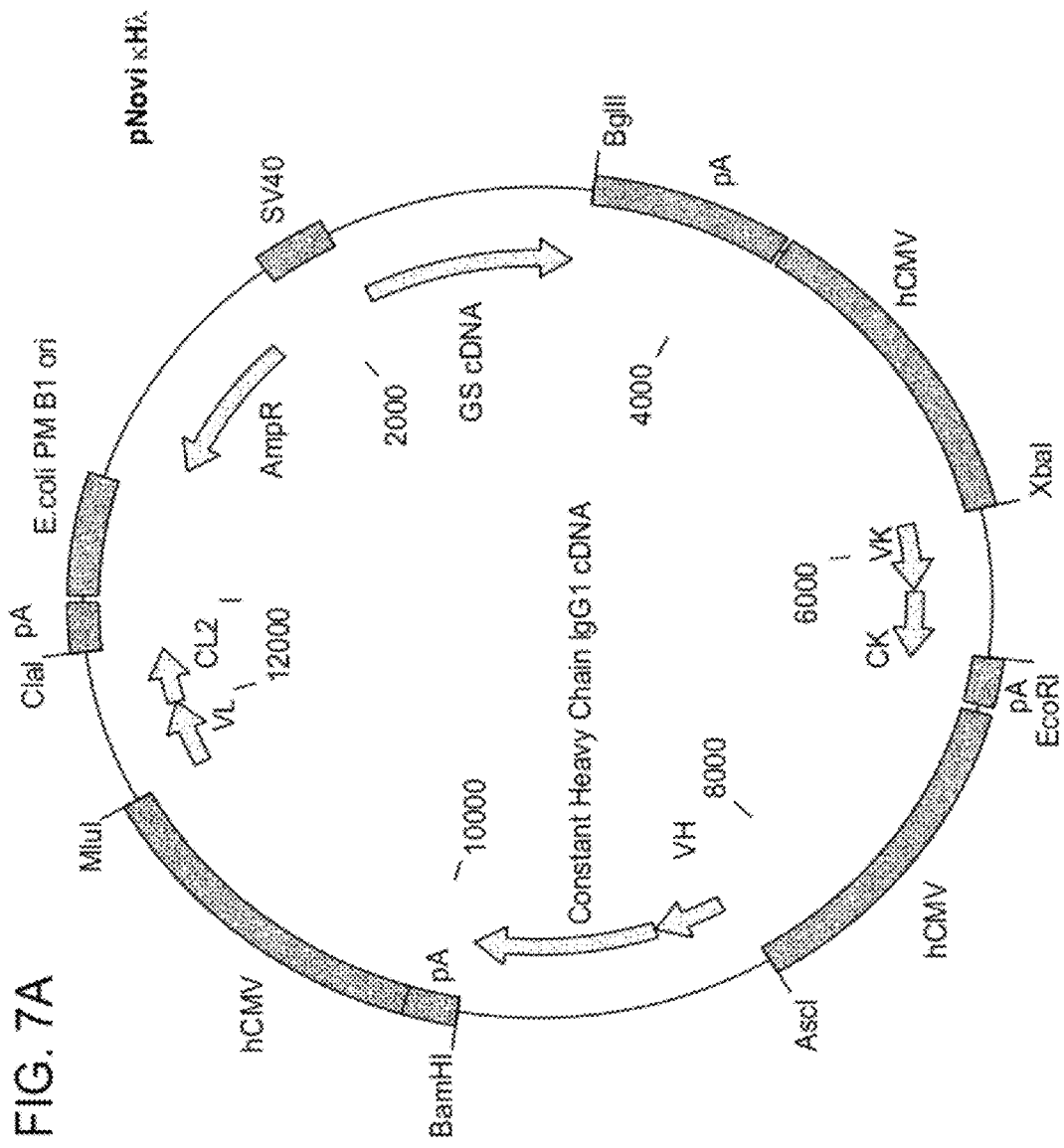
FIG. 7 is a schematic representation of vectors used for the co-expression of one heavy chain and two light chains in mammalian cells. Both vectors contain three promoters to drive gene expression, a glutamine synthetase gene for stable cell line selection. In the second vector, pNovI κHλκ, the expression of an additional Kappa light is driven by an internal ribosome entry site (IRES). The different genes and genetic control elements are indicated. hCMV, human cytomegalovirus promoter; SV40, V40 promoter; pA polyadenylation signal; VH, heavy chain variable domain; VK, light chain variable Kappa domain; CK light chain constant Kappa domain; VL, light chain variable Lambda domain; CL2, light chain constant Lambda domain2; GS cDNA, Glutamine Synthetase cDNA; AmpR; selectable marker for Ampicilin resistance. A selected number of restriction sites are indicated.
Figure 7B:
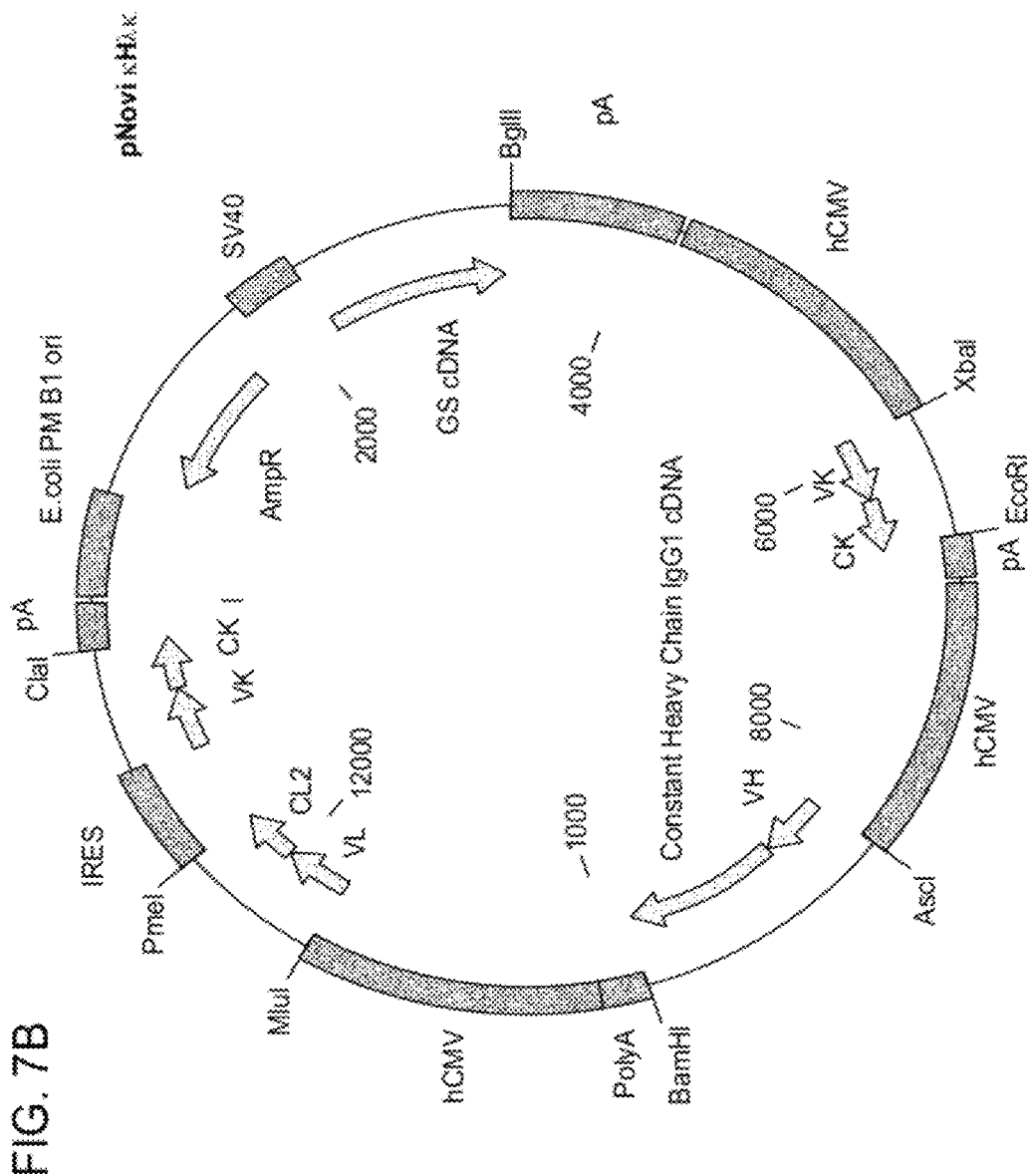

Co-Expression of a Single Heavy Chain and Two Light Chains in Mammalian Cells The simultaneous expression of one heavy chain and two lights chain in the same cell can lead to the assembly of three different antibodies (FIG. 8A). Simultaneous expression can be achieved in different ways such as that the transfection of multiple vectors expressing one of the chains to be co-expressed or by using vectors that drive multiple gene expression. A vector pNovi κHλ was designed to allow for the co-expression of one heavy chain, one Kappa light chain and one Lambda light chain (FIG. 7A). The expression of the three genes is driven by human cytomegalovirus promoters (hCMV) and the vector also contains a glutamine synthetase gene (GS) that enables the selection and establishment of stable cell lines. Another vector, pNovi κHλκ, was also constructed, in which a second copy of a Kappa light chain was inserted after the Lambda light chain and its expression was driven by an internal ribosome entry site (IRES). Using this bicistronic design, the relative expression of the Kappa light chain can be increased. The two vectors are schematically represented in FIG. 7.

Example 7

Figure 8B:
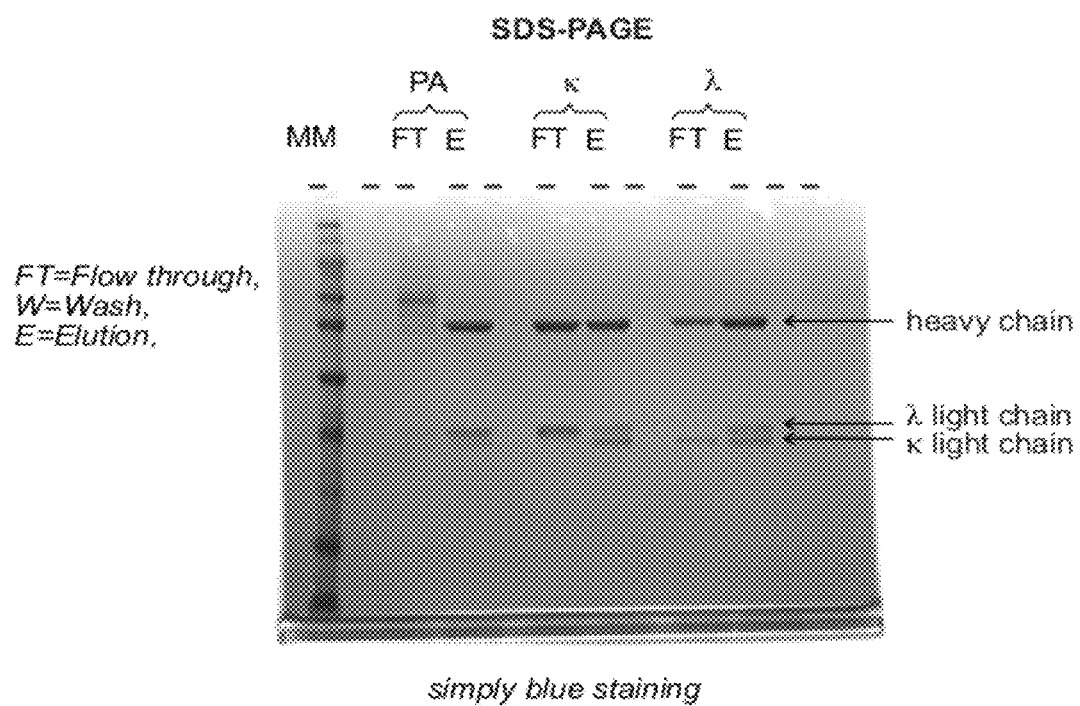
FIG. 8B is an illustration depicting co-expression, purification and SDS-PAGE analysis of bispecific antibodies of the invention. The gel was stained using simply blue. PA: Protein A; K: Kappaselect; λ: Lambda selected; FT: column flow-through; E: elution fraction.

Transient Co-Expression of a Single Heavy Chain and Two Light Chains in Mammalian Cells and Purification of Total IgG The VH and VL gene of the anti-INFγ IgGλ or the anti-IL6RC IgGκ were cloned in the vector pNovi κHλ described in Example 5, for transient expression in mammalian cells. Peak cells were cultured in 6-well plates at a concentration of $6 \times 10^5$ cells per well in 2 ml culture media containing fetal bovine serum. 2 μg of plasmid DNA was transfected into the cells using TransIT-LT1 transfection reagent (Mims) according to manufacturer's instructions. One day following transfection, the culture media was aspirated, and 3 ml of fresh serum-free media was added to cells and cultured for five days at 37° C. Following a five days culture period, the supernatant was harvested, centrifuged at 4000 rpm and applied on MabSelect Sure PA resin (GE Healthcare) according to manufacturer's instructions. Total IgGs were eluted under acidic condition followed by neutralization and buffer exchange into PBS. The IgG content was quantified by absorption at 280 nm and analyzed by SDS-PAGE. The presence of two bands corresponding to the two light chains and one band corresponding to the heavy chain indicated that the three chains could be expressed simultaneously in the same cell (FIG. 8B).

Example 8

Purification of Bispecific Antibodies Carrying a Lambda and a Kappa Light Chain

The co-expression of one heavy chain and two light chains in the same cells can lead to the assembly of three different antibodies: two monospecific antibodies bearing the same light chain on both arms and a bispecific antibody bearing a different light chain associated with the heavy chain on each arm. The later can be isolated from the monospecific antibodies by chromatography techniques that take advantage of the different biochemical properties of the monospecific and bispecific antibodies. In order to develop a generic purification approach that is applicable to all bispecific antibodies generation, we used an affinity chromatography approach schematically depicted in FIG. 8A. Culture supernatants from transfected cells were applied to MabSelect Sure PA resin (GE Healthcare) column and total IgG purified as described in Example 7. The total IgG was then applied to a column containing CaptureSelect Fab Kappa affinity matrix (BAC BV, Holland) equilibrated with ten column volumes of PBS. The column was then washed with 5-10 column volumes of PBS. The Immunoglobulin molecules bearing a Kappa light chain were eluted from the column by applying 5 column volumes 0.1 M Glycine pH 2.0 and fractions were collected and neutralized. The fractions containing the antibody were pooled before buffer exchange on a PD10 desalting column (Amersham) equilibrated with PBS. The antibody was then applied on a second column containing CaptureSelect Fab Lambda affinity matrix equilibrated with ten volumes of PBS. The column was then washed with 5-10 column volumes of PBS. The Immunoglobulin molecules bearing only Kappa light chain do bind to the column and were found in the flowthrough. Antibodies carrying a Lambda light chain were eluted from the column by applying 5 column volumes 0.1 M Glycine pH 3.0 and fraction were collected. The fractions containing the bispecific antibody were pooled before buffer exchange on a PD10 desalting column (Amersham) equilibrated with PBS. The Immunoglobulin molecules bearing a Kappa light chain were eluted from the column by applying 5 column volumes 0.1 M Glycine pH 2.0 and fractions were collected and neutralized. The fractions containing the antibody were pooled before buffer exchange on a PD10 desalting column (Amersham) equilibrated with PBS. The antibody was then applied on a second column containing CaptureSelect Fab Lambda affinity matrix equilibrated with ten volumes of PBS. The column was then washed with 5-10 column volumes of PBS. The Immunoglobulin molecules bearing only Kappa light chain do bind to the column and were found in the flowthrough. Antibodies carrying a Lambda light chain were eluted from the column by applying 5 column volumes 0.1 M Glycine pH 3.0 and fraction were collected. The fractions containing the bispecific antibody were pooled before buffer exchange on a PD10 desalting column (Amersham) equilibrated with PBS. The flow through and elution fraction of each purification step was analyzed by SDS-PAGE and indicated that the antibodies bearing Lambda light chains were found in the flow through of the CaptureSelect Fab Kappa affinity matrix and, conversely, that antibodies bearing Kappa light chains were found in the flow through of the CaptureSelect Fab Lambda affinity matrix (FIG. 8B). As expected, in the final elution fraction, the intensity of the bands corresponding to the two light chains is equivalent. Thus this three step approach allows for the purification of bispecific antibodies bearing both a Kappa and a Lambda light chain. The final recovery of bispecific antibody bearing a Kappa and Lambda light chain was approximately 10-21% in different experiments. The Protein A elution fraction also indicated that more Lambda light chain that Kappa light chain is assembled into the purified IgG suggesting that increased expression of Kappa light chain could increase the assembly and recovery of bispecific antibody.

Example 9

Modulation of Light Chain Expression to Optimize Bispecific Antibody Assembly

Figure 9:
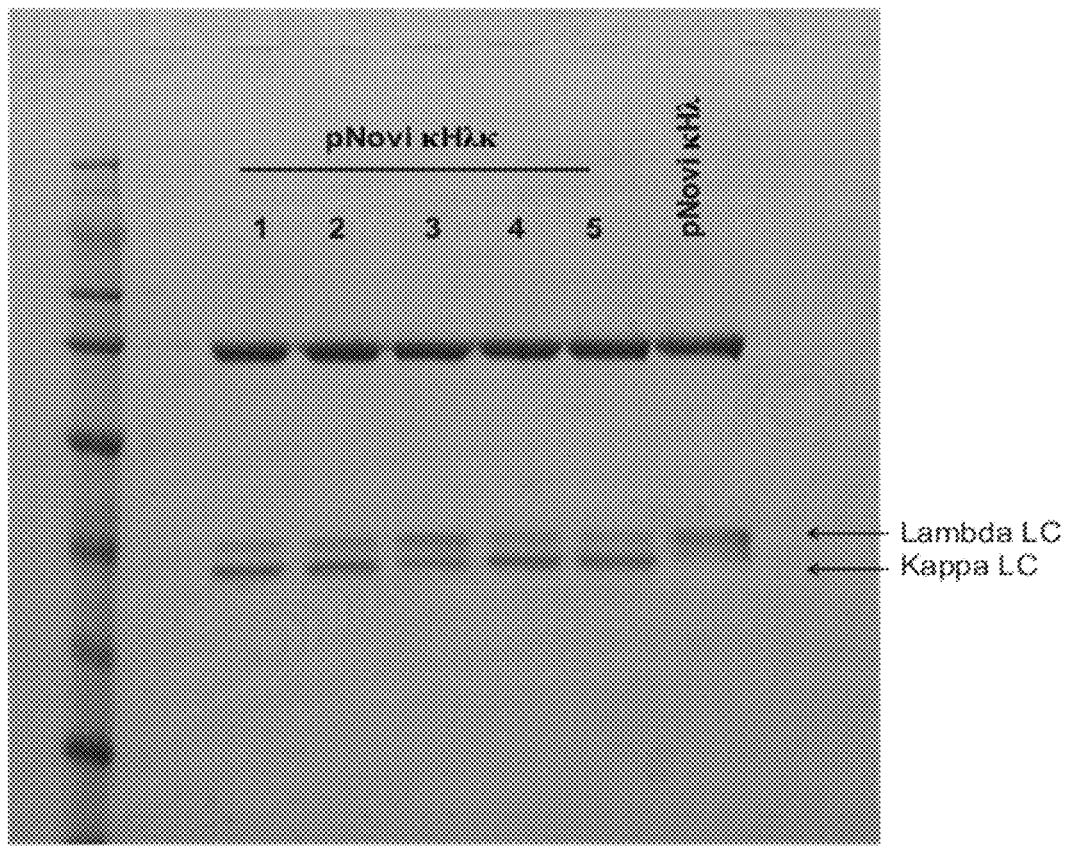
FIG. 9 is an illustration of an SDS-PAGE analysis of total IgG purified from mammalian cells transfected with vectors enabling different levels of Kappa light chain expression using different IRES elements within the pNovI κHλκ vector (lane 1-5) and compared to the pNovI κHλ vector. The relative intensities of the Kappa and Lambda light chain indicate that the expression levels can be modulated.

In order to increase the expression of the Kappa light chain, the common VH gene, the VLambda gene of the anti-INFγ antibody and two copies of VKappa of the anti-IL6RC were cloned in the vector pNovi κHλκ described in Example 6. The expression of the second copy of the VKappa light chain is driven by and IRES. Different IRES elements were tested to achieve different levels of VKappa light chain expression. This resulted in the construction of five independent vectors: pNovi κHλκ 1 to 5. These vectors were used for transient transfections in mammalian cells as described in Example 7 and total IgG were purified form the supernatant using Protein A affinity purification. The SDS-PAGE analysis indicates that the different pNovi κHλκ vectors increased the expression and assembly of the Kappa light chain into the IgG compared to expression using the pNovi κHλ vector (FIG. 9). The total IgG fractions obtained after Protein A purification for each of these constructs was further purified in two consecutive steps using CaptureSelect Fab Kappa and CaptureSelect Fab Lambda as described in Example 8. The yield in bispecific antibodies was 20% for the pNovi κHλ and ranged between 33 and 41% for pNovi κHλκ constructs, indicating that increased Kappa light chain expression lead to increased bispecific antibody assembly. To further confirm these findings, co-transfections suing pNovi κHλ and the vector expressing the monospecific anti-IL6RC IgGκ were performed. In this way the relative levels of Kappa light chain as well as the yields of bispecific antibody were also increased indicating that several approaches can be taken to adjust the relative light chain expression.

Example 10

Characterization of the Purified Bispecific Antibody

The purified bispecific antibodies isolated as described in the Examples above were characterized using different techniques.

Isoelectric focusing gel (IEF). The purified bispecific antibodies isolated as described in Example 9 were analyzed using an IsoGel Agarose IEF plates with a range of pH 3-10 (Lonza) and compared to the monospecific anti-INFγ IgGλ and the anti-IL6RC IgGκ antibodies. After focusing, the gel was placed in fixative solution for 30 mins, washed with water for 5 min and then dried at RT. Gel was stained with Coomassie staining for 15 min, briefly rinsed with water and with destaining solution for 2×15 min. Finally gel was dried at RT before imaging. The results shown in FIG. 10A indicate that the IgGκλ bispecific antibody has a different and intermediate pI compared to the pI of the two monospecific antibodies as predicted from the antibody format and theoretical calculations. The staining also demonstrated that the bispecific antibody is highly pure after the three step purification process described in Example 8.

Figure 10B:
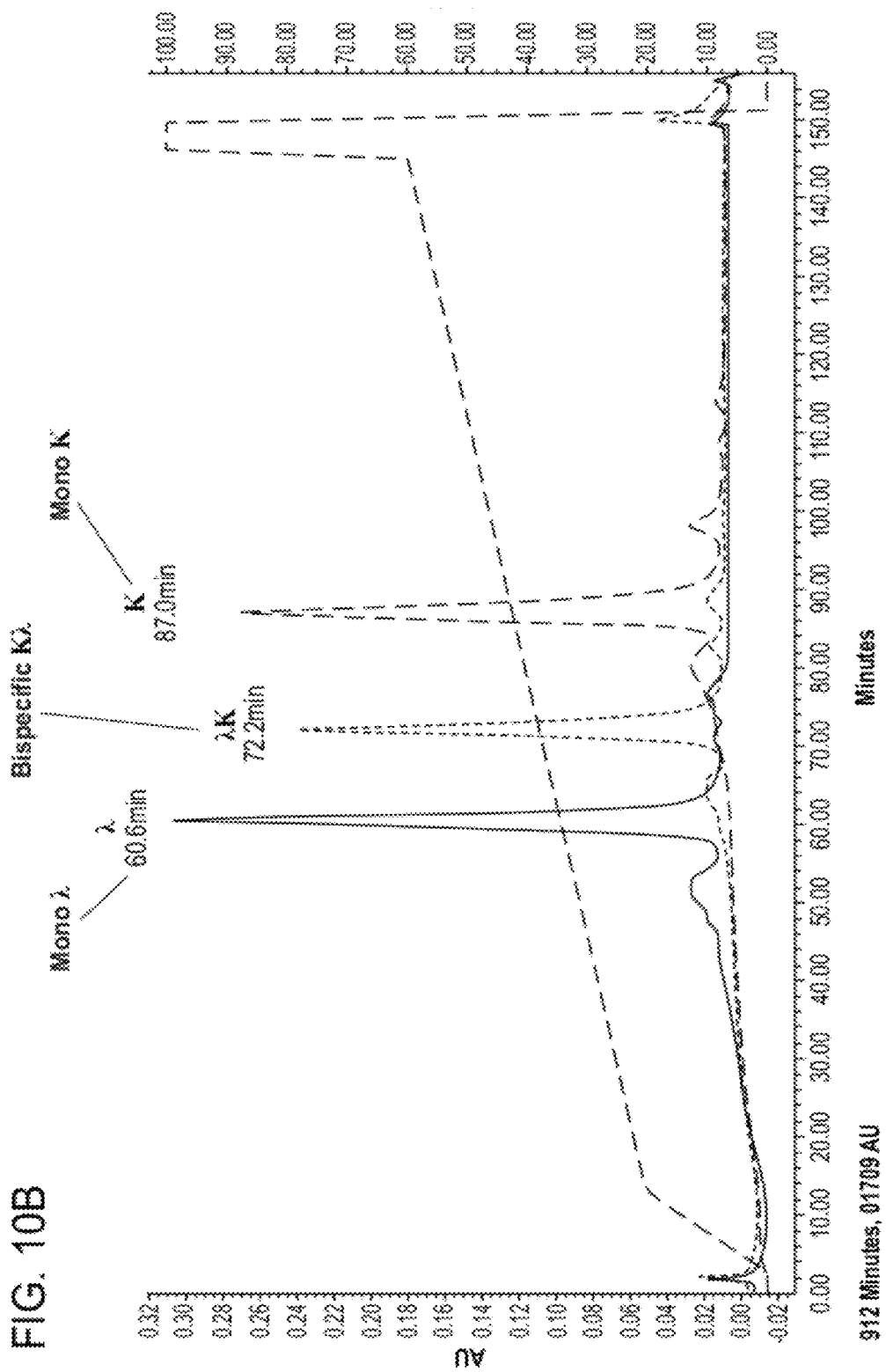
FIG. 10B is an illustration of IEX-HPLC analysis of monospecific and bispecific antibodies. The three antibodies were injected independently and their elution profile are overlaid in the graph. The gradient used in the experiment is shown.

Ion exchange chromatography (IEX). 50 μg of purified monospecific and bispecific antibodies were analyzed by Ion Exchange-High Performance Liquid Chromatography (IEX-HPLC) (HPLC Waters e2695/detector 2489) using an Agilent column Bio Mab, NP5, (Agilent): the mobile phases were: A: Na2HPO4/NaH2PO4 10 mM, pH6.5; B: Na2HPO4/NaH2PO4 10 mM, NaCl 100 mM, pH6.5; using a flow of 0.8 mL/min and 20%-60% gradient over 133 minutes. The three antibodies have different retention times with the peak corresponding of the bispecific antibody having an intermediate profile compared to the monospecific antibodies (FIG. 10B).

ELISA. The monospecific anti-INFγ IgGλ, the anti-IL6RC IgGκ and the bispecific IgGκλ antibodies were tested by ELISA for binding to INFγ and IL6RC. The results shown in FIG. 11 indicate that the bispecific IgGκλ is able to bind to both target and is can be detected with both anti-human Cλ and anti-human Cλ secondary antibodies.

Surface Plasmon Resonance (SPR). The affinity and binding kinetics of monospecific anti-INFγ IgGλ, the anti-IL6RC IgGκ and the bispecific IgGκλ antibodies were characterized on a Biacore 2000 instrument (Biacore AB, Uppsala, Sweden). 200RU of a goat anti-human polyclonal IgG (ahIgG; Biacore) were immobilized by EDC/NHS chemistry on a CM5 Biacore chip. This surface was used to capture monospecific or bispecific human IgG. The surface was regenerated after each cycle by injection of 10 mM glycine pH=1.5 at 30 μL/min, for 30s followed by 1 min of stabilization time in HBS-EP buffer. The data was fitted according to 1:1 Langmuir model and the $K_{on}$, $K_{off}$ and $K_D$ values determined (Table III). Similar affinity values were obtained for the monospecific antibodies and the bispecific IgGKX antibodies. The data indicates that the two antibody combining sites bind to hIFNγ and IL6RC similarly in a monospecific and bispecific format.

Figure 11A:
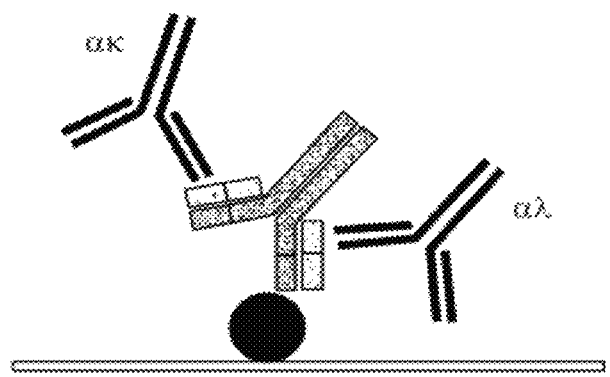
FIG. 11A is a schematic representation of the ELISA format.
Figure 11B:
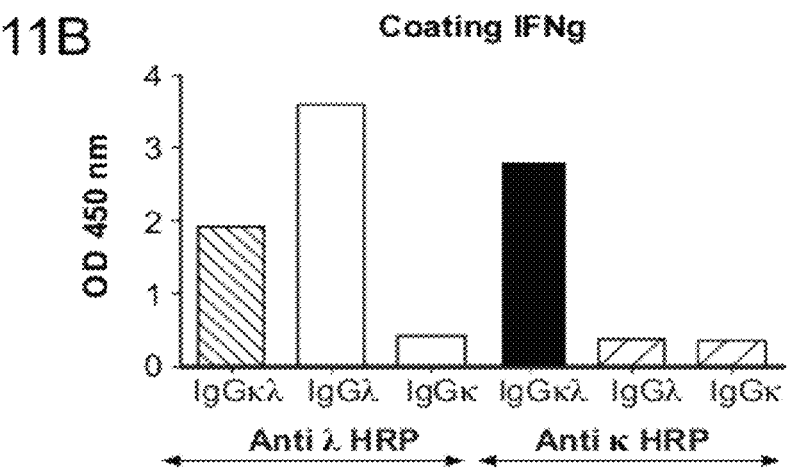
FIG. 11B is a graph depicting the results of the ELISA with INFγ immobilized on the plate.
Figure 11C:
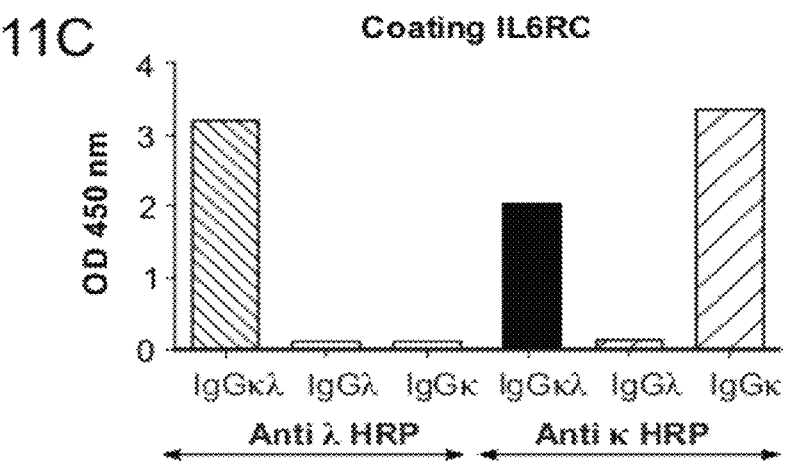
FIG. 11C is a graph depicting the results of the ELISA with IL-6RC immobilized on the plate. IgGκ, anti-IL6RC monospecific antibody; IgGλ, anti-INFγ monospecific antibody; IgGκλ, anti-IL6RC/anti-INFγ bispecific antibody. Secondary detection antibodies anti-human Lambda HRP and anti-Human Kappa HRP are indicated.

The capacity of the bispecific IgGκλ to interact with both targets simultaneously was tested by SPR. Biotinylated INFγ was immobilized on streptavidin coating CM5 Biacore chip. The monospecific and the bispecific antibodies were injected on this surface followed by injection of IL6RC. The sensorgram shown in FIG. 11A show that the bispecific IgGκλ antibody was able to bind to immobilized INFγ and was able to capture IL6RC simultaneously. SPR was also used to assess the relative amounts of Kappa and Lambda light chains in the purified bispecific antibody. IgGκλ was directly immobilized via amine coupling on the surface of a CM5 Biacore chip and an anti-human CKappa antibody was injected followed by an anti-human CLambda antibody at the same concentration. Equivalent responses were obtained with both anti-light chain antibodies indicating that, as predicted by the format, equivalent amounts of Kappa and Lambda light chains are present in the bispecific IgGκλ antibody (FIG. 12B)

TABLE III

Binding kinetic analysis for monospecific and IgGκλ bispecific antibodies for IFNγ and IL6RC measured on a Biacore 2000 system.

| Analyte | Ligand | KD (M) | $k_{on}$ (1/Ms) | $k_{off}$ (1/s) |
|---|---|---|---|---|
| IFNγ | IgGκλ | 1.84E−10 | 9.19E+05 | 1.69E−04 |
|  | IgGλλ | 1.96E−10 | 6.08E+05 | 1.19E−04 |
| IL6RC | IgGκλ | 2.72E−07 | 7.44E+03 | 2.02E−03 |
|  | IgGκκ | 2.66E−07 | 8.08E+03 | 2.15E−03 |

Example 11

Manufacturing of Bispecific IgGκλ Antibodies

The expression of IgGκλ bispecific antibody was also performed in Chinese Hamster Ovary (CHO) cells that are widely used for the manufacturing of monoclonal antibodies. In the example presented herein both semi-stable pools of transfected CHO cells as well as stable cell CHO lines were generated for the production of IgGKX bispecific antibodies. In the studies presented herein, stable CHO lines were generated and grown using a chemically defined, animal component-free (CDACF) manufacturing process. The overall process is depicted in FIG. 13.

Figure 14A:
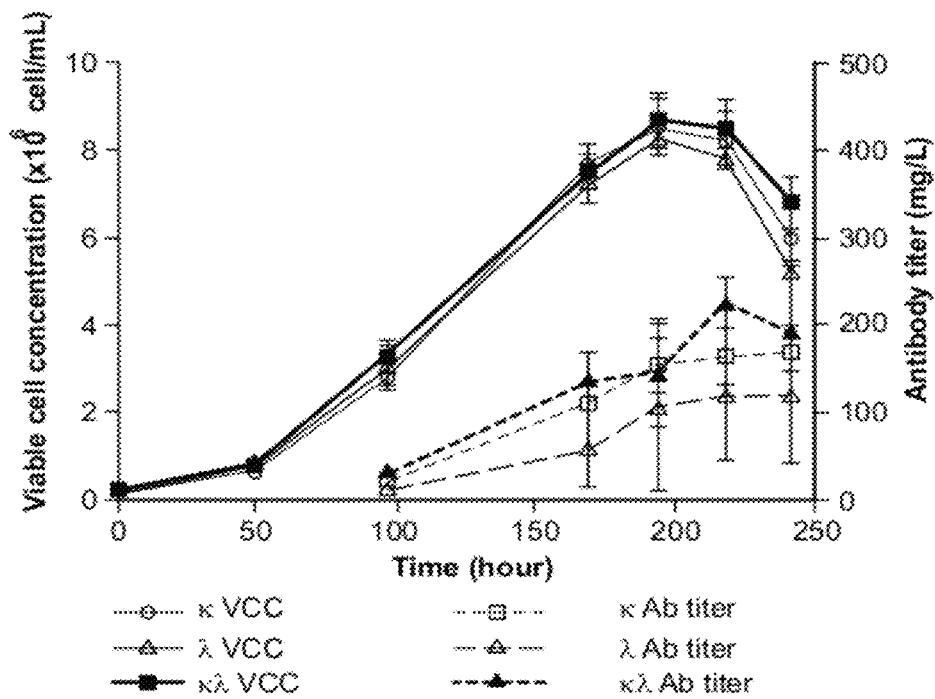
FIG. 14A is a graph depicting the growth and antibody production profiles of pools of CHO cells at a small-scale production level in an Erlenmeyer flask. Antibody production levels were determined by Protein A-HPLC analysis. VCC stands for viable cell concentration and Ab stands for antibody.
Figure 14B:
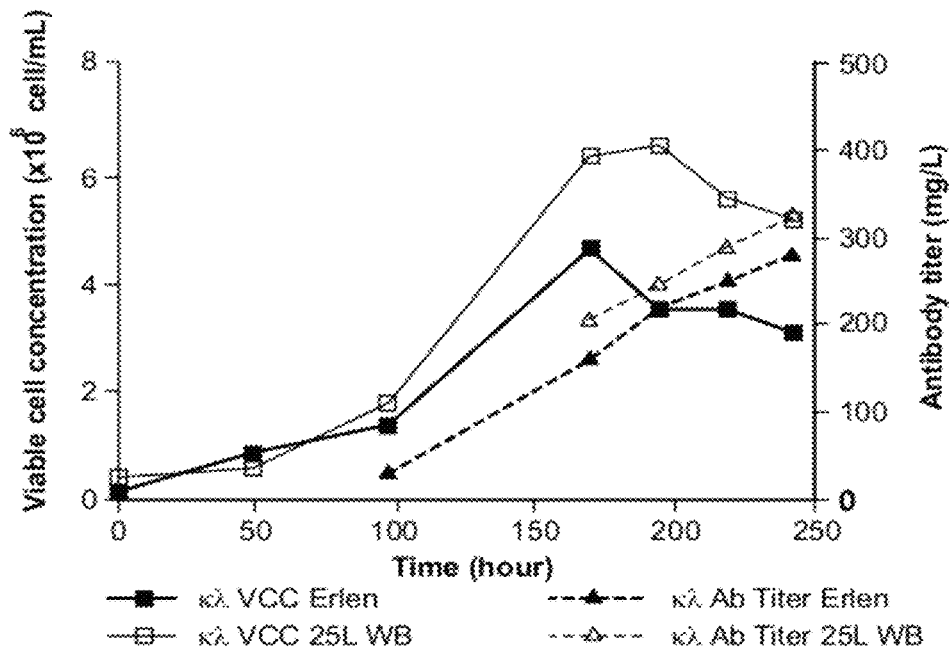
FIG. 14B is a graph depicting the growth and antibody production profile comparison between small-scale and mid-scale fermentation. Antibody production levels were determined by Protein A-HPLC analysis. VCC stands for viable cell concentration and Ab stands for antibody.

CHO pools. CHO cells were electroporated with the linearized vector pNovi KHXK encoding the IgGκλ anti-INFγ/anti-IL6RC bispecific antibody described in the Examples above as well as with plasmids driving the expression of the monospecific anti-INFγ IgGλ and the anti-IL6RC IgGκ. After electroporation, pools of transfected cells were grown in non-fed 10 day overgrown conditions. The cells transfected with bispecific construct presented similar growth profiles as compared to the cells transfected with monospecific expression vectors. In addition, the productivities were also comparable and reached a typical range of antibody productivity: between 100-200 mg/L for non-fed overgrown pool cultures (FIG. 14A). Scaling up between small-scale production in an Erlenmeyer flask (100 mL) and mid-scale production in a 25 Wave Bag was successfully achieved (FIG. 14B). These results indicate that similar growth curves and productivities are obtained during expression of bispecific IgGκλ antibody in CHO cell lines and the corresponding monospecific antibodies.

Figure 15A:
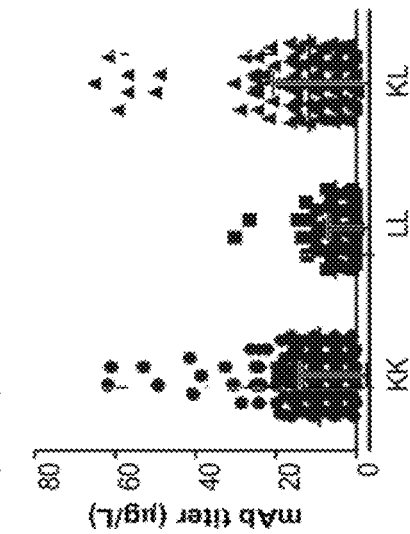
FIGS. 15A and 15 B are a series of graphs depicting antibody productivity in a 96 well plate (96wpl) of mono Kappa (KK), mono Lambda (LL) and bispecific Kappa Lambda (KL) antibody expressing cell lines five weeks post-transfection in two independent experiments. Antibody production levels were determined by ELISA. mAb stands for monoclonal antibody.
Figure 15B:
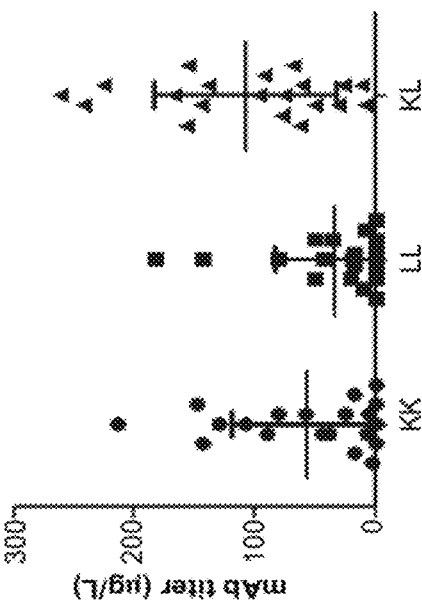
FIGS. 15C and 15D are a series of graphs depicting antibody productivity in shaken 24 well plate (24wpl) overgrown batch cultures of mono Kappa (KK), mono Lambda (LL) and bispecific Kappa (KL) antibody.
Figure 15C:
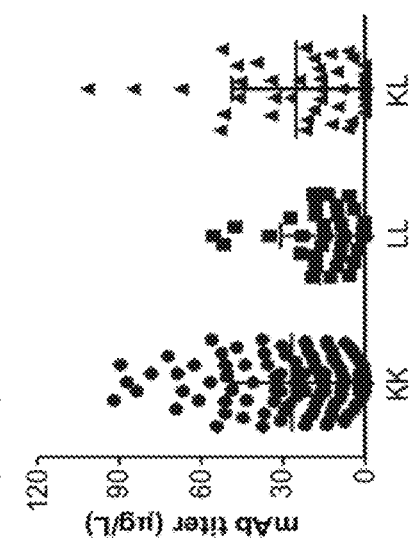
Figure 15D:
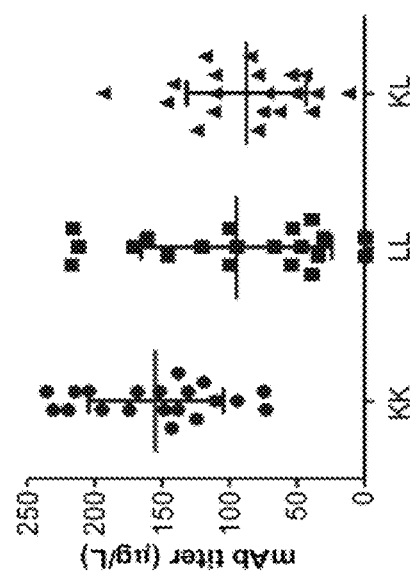

Stable CHO cell lines. Recombinant cell lines producing bispecific antibody were generated by electroporation of CHO cells with the pNovi κHλκ vector. Post transfection, recombinant cell lines were selected by diluting the cell culture in the presence of a final concentration of 50 μM methionine sulphoximine (MSX). After 6 weeks of incubation, colonies of recombinant cell lines were screened for total IgG productivity by FastELISA® (R&D Biotech) (FIG. 15A-B). Selected cell lines were expanded in cell culture medium containing 25 μM MSX, transferred to 24 wells microtitre plates and screened for productivity and growth characteristics in suspension culture (FIG. 15C-D). The results revealed that the IgGκλ bispecific antibody can be produced in shaken batch overgrown conditions at a level comparable to cell lines expressing standard monospecific antibodies. Top producing cell lines were selected and operated in 50 mL batch overgrown cultures in shake flasks for a maximum of 10 days. Protein A HPLC was used for total IgG quantification in the supernatant. Total IgG from the supernatants of the 10 top producing cell lines were purified by by MabSelect SuRE chromatography using 1 mL HiTrap (GE Healthcare) prepacked columns. The relative amounts of monospecific and bispecific antibodies in the total purified IgG was assessed by IEX-HPLC as described in Example 10. For the majority of the cell lines, the fraction of IgGκλ bispecific antibody varied between 37-42% of the total IgG and two cell lines had expressed lesser amounts of IgGκλ (22 and 25%). The results for the 10 CHO cells lines are summarized in Table IV.

TABLE IV

| | Total antibody titre (mg/mL) | Total antibody post MabSelect SuRr purification (mg) | Bispecific antibody relative quantity from IEX-HPLC (%) | Total bispecific antibody quantity (mg) |
|---|---|---|---|---|
| Cell line 1 | 0.35 | 10.73 | 37 | 3.97 |
| Cell line 2 | 0.32 | 9.54 | 25 | 2.37 |
| Cell line 3 | 0.31 | 10.02 | 37 | 3.72 |
| Cell line 4 | 0.42 | 10.01 | 40 | 4.00 |
| Cell line 5 | 0.38 | 11.59 | 38 | 4.39 |
| Cell line 6 | 0.43 | 11.10 | 43 | 4.75 |
| Cell line 7 | 0.49 | 12.67 | 42 | 5.32 |
| Cell line 8 | 0.33 | 8.96 | 22 | 2.01 |
| Cell line 9 | 0.38 | 9.94 | 42 | 4.18 |
| Cell line 10 | 0.39 | 10.98 | 42 | 4.61 |

Purification and characterization of IgGκλ bispecific antibody expressed in CHO. The supernatant of CHO cell pools transfected with bispecific and monospecific constructs were used for purification. The monospecific anti-INFγ IgGλ, and the anti-IL6RC IgGκ were purified using Protein A affinity chromatography and desalted into PBS, whereas the bispecific IgGκλ antibodies were purified using the three step affinity chromatography process described in Example 8. The elution fractions and flow through of the different steps as well as the final purified samples were analyzed by SDS-PAGE and IEF (FIG. 16). The specificity of the IgGκλ was monitored after each purification step by ELISA (FIG. 17). The results demonstrate that the purification process was robust and compatible with expression in CHO and yield highly pure IgGκλ bispecific antibody.

Example 12

Additional Examples of Bispecific IgGκλ Antibodies

Figure 18:
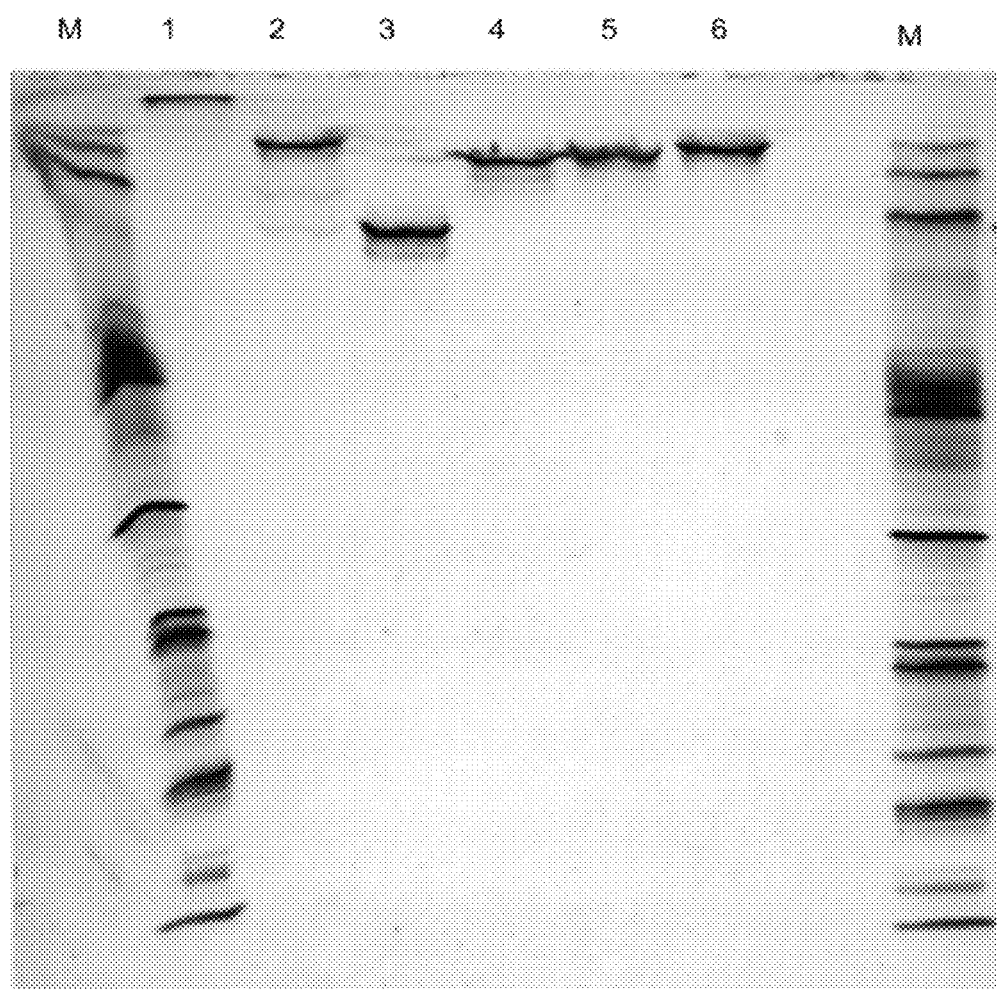
FIG. 18 is an illustration of an IEF gel of different monospecific and bispecific antibodies, indicating that the difference in pI can vary depending on the antibody light variable sequence. Lane 1, anti-NusA IgGκ; Lane 2, anti-NusA/anti-INFγ IgGκλ; Lane 3, anti-INFγ IgGλ; Lane 4, anti-IL6RC IgGκ; Lane 5, anti-IL6RC/anti-IL6RC IgGκλ; Lane 6, anti-IL6RC IgGλ.

Other examples of IgGκλ bispecific antibodies were isolated, expressed and purified as described in the Examples above. These included an anti-NusA/anti-INFγ IgGκλ bispecific antibody and an anti-IL6RC/anti-IL6RC IgGκλ bispecific antibody in which both combining sites bind to IL6RC but carry a Kappa and a Lambda light chain. These purified bispecific antibodies were analyzed by IEF along with their respective monospecific counterparts (FIG. 18). The results show that the pI of the bispecific antibody is always intermediate between the pI of the monospecific antibodies but that the differences can vary significantly depending on sequence the light chain variable domain. This illustrates that purification of the bispecific antibody based on charge differences might be difficult if the two light chains have similar biochemical properties and highlights the advantage of the affinity purification approach of the invention.

Example 13

Figure 19A:
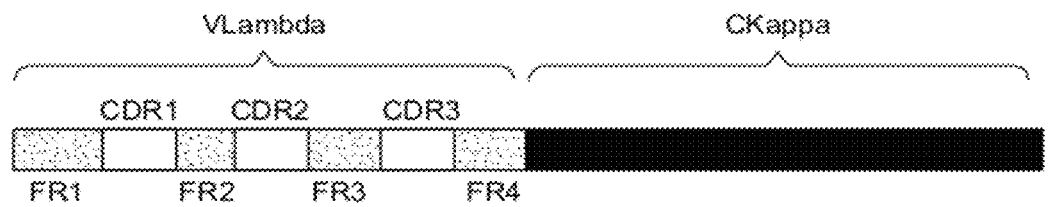
FIG. 19 is a schematic representation of three different hybrid proteins obtained by combining a variable Lambda gene and a Kappa constant gene. The fusion points differ between the different hybrids: in 19A, VLambda fused to CKappa; in 19B, VLambda up to CDR3 fused to VKappa FR4 and CKappa; and in 19C, VLambda and the first four amino acids of CLambda and CKappa excluding the first four amino acids. CDR, Complementary Determining Region; FR, Framework region.
Figure 19B:
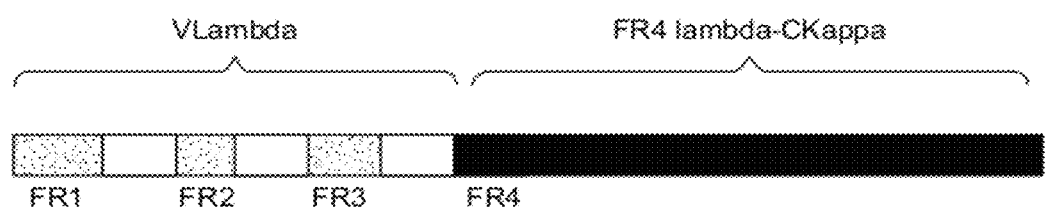
Figure 19C:
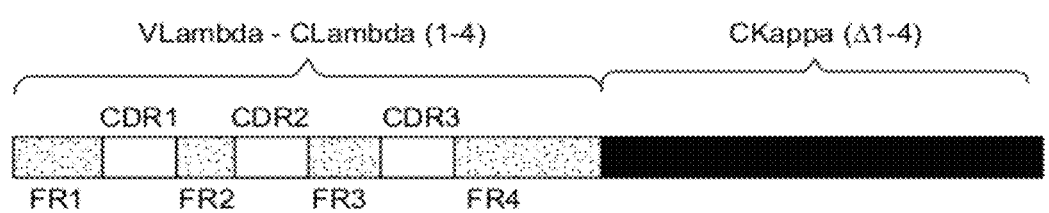
Figure 20:
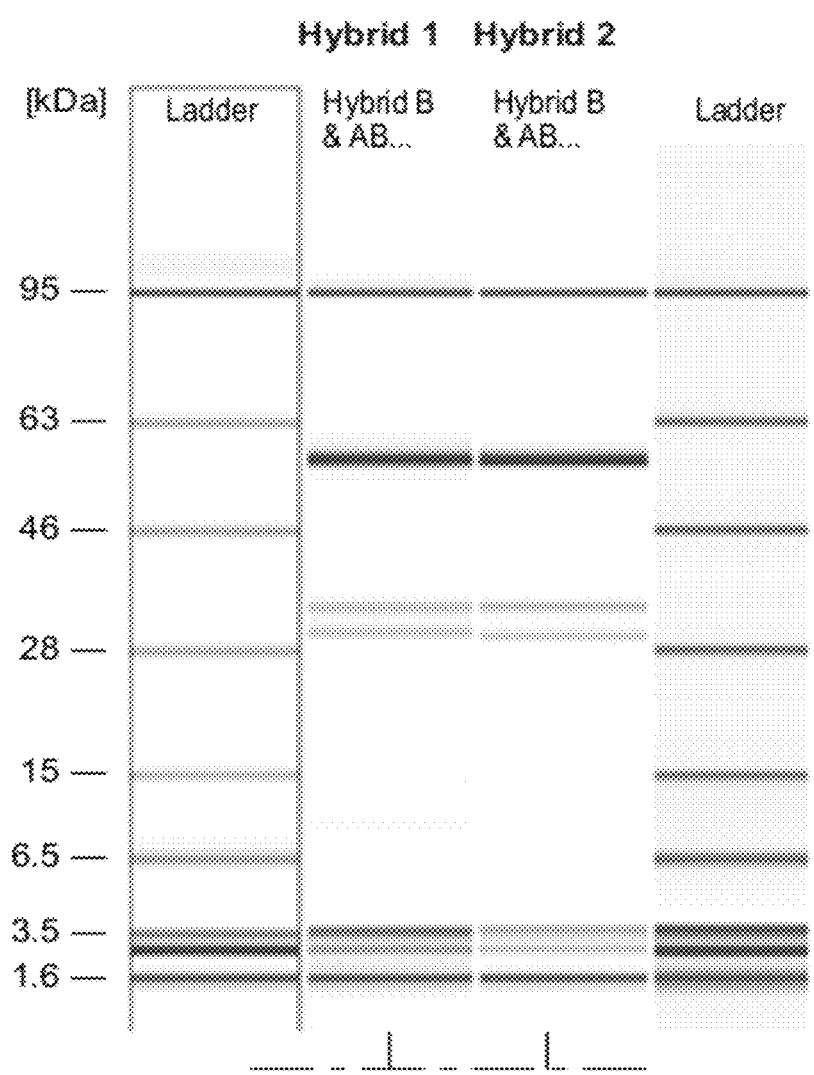
FIG. 20 is an illustration of the analysis of two hybrid light chain constructs on a Bionalyzer 2100 system using a Protein 80 chip (Agilent Technologies). The electropherogram corresponding to the gel image are indicated.
Figure 20:
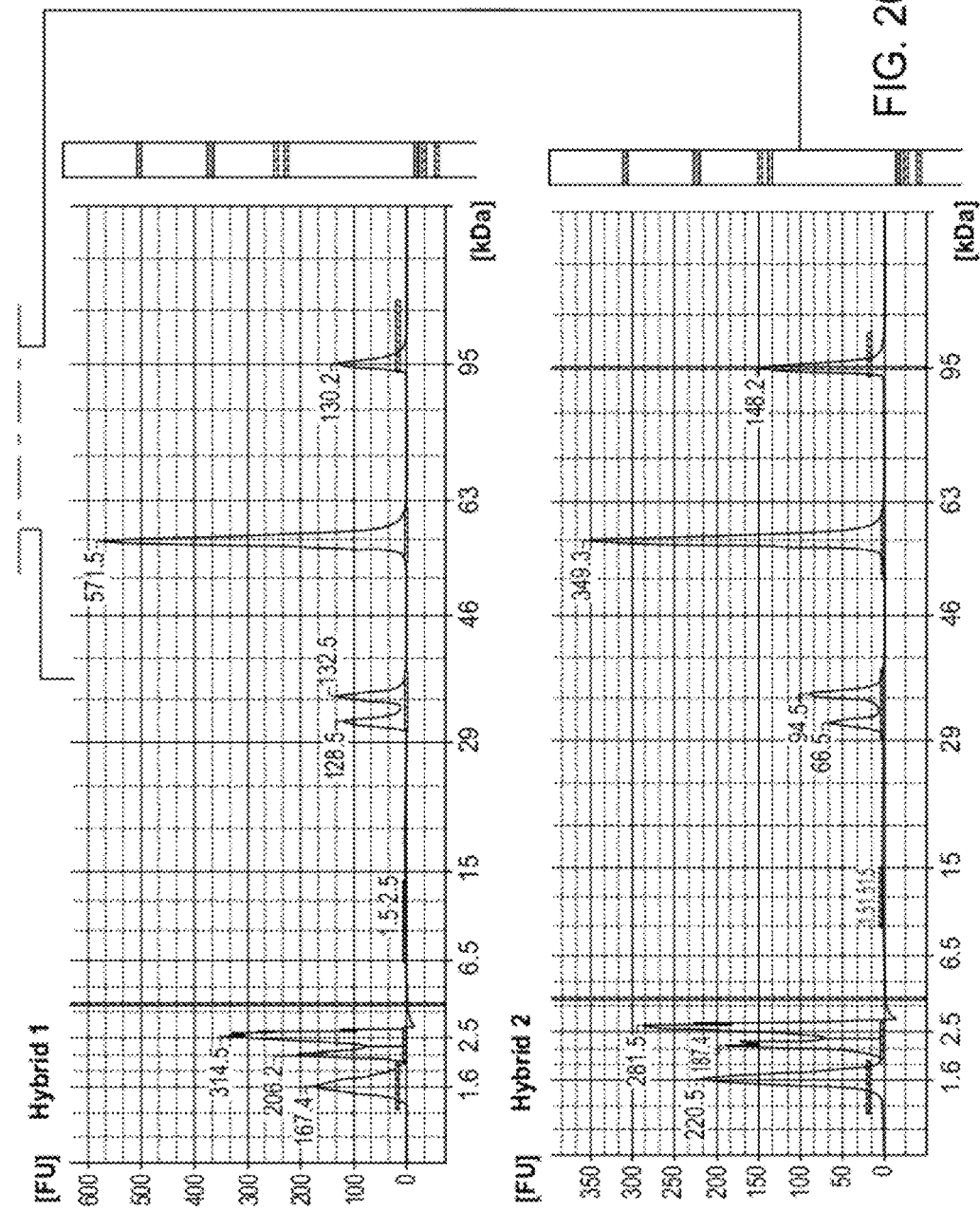

Generation of Bispecific IgGκλ antibodies using two Kappa or Two Lambda Variable Domains Bispecific antibodies can also generated using two variable domains of the same type (Lambda or Kappa). As the affinity purification steps require the presence of the constant Kappa and constant Lambda domains of the light chains, any light chain variable domain can in principle be fused to these constant domains to generate hybrid light chains as illustrated in FIG. 3. This was demonstrated by using two antibodies directed against INFγ and IL6RC isolated from fixed VH antibody libraries described in Example 1. In this case both antibodies share the same VH and have a Lambda light chain variable domain. The VLambda domain of the anti-INFγ antibody was combined to the Lambda constant domain whereas the VLambda domain of the anti-IL6RC antibody was combined with the Kappa constant domain. For the latter, three different constructs were generated including different fusion points between the VLamda domains and the CKappa domain. In one construct (Hybrid 1) the fusion point was at the end of framework 4 (FR4) region of the VLambda domain and include the whole the Constant Kappa domain (FIG. 19A). In another construct (Hybrid 2), the Lambda FR4 region was replaced by a Kappa FR4 region (FIG. 19B). In the third construct (Hybrid 3), the first 4 amino acids of the Constant Kappa domain were substituted by the 4 amino acids of the Constant Lambda domain (FIG. 19C). These different hybrid Lambda-Kappa light chains were cloned along with the common heavy chain and Lambda light chain into the pNovi κHλ vector. Mammalian cell transfection, protein expression and three step affinity purification of the IgGκλ were performed as described in the Examples above. Analysis of the elution fractions indicated that the Hybrid 3 light chain did not bind to the Kappaselect resin and therefore did not allow for efficient bispecific antibody purification. The Hybrid 1 and Hybrid 2 allowed for efficient IgGκλ bispecific purification. These purified IgGκλ bearing a hybrid light chain analyzed on an Agilent Bionalyzer 2100 using a Protein 80 chip (Agilent Technologies) and the peaks on the electropherogram corresponding to the light chains were shown to be equivalent (FIG. 20). The results show that bispecific antibodies of the invention can be generated using two antibodies having a common heavy chain and two light chains having Variable domains of the same type (Kappa or Lambda).

Example 14

Both VH and VL of the Described Antibodies are Involved in Antigen Binding

Figure 21A:
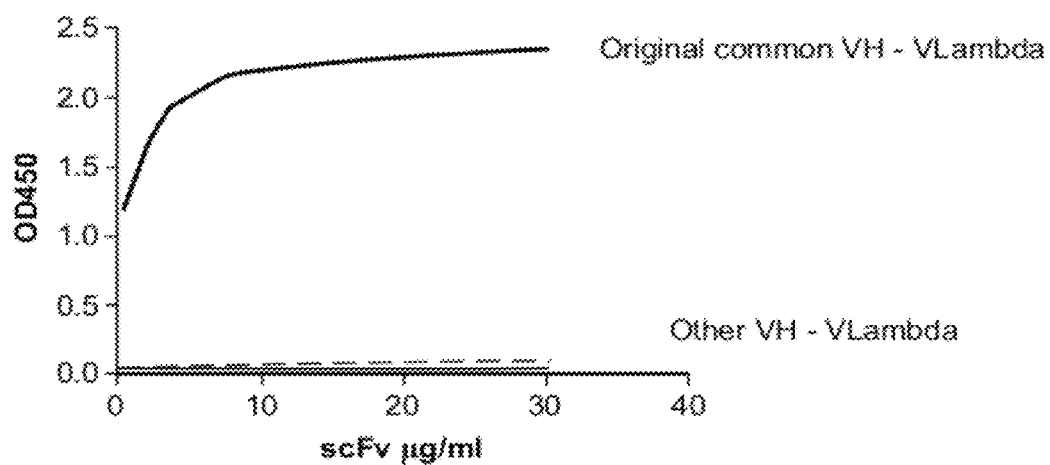
FIG. 21 is a series of graphs depicting the results of dose response ELISA using scFv specific for INFγ (A) or IL6RC (B) in which the VH domain was either the common VH originally selected (top curves) or other VH domains that allow scFv expression and purification (bottom curves).
Figure 21B:
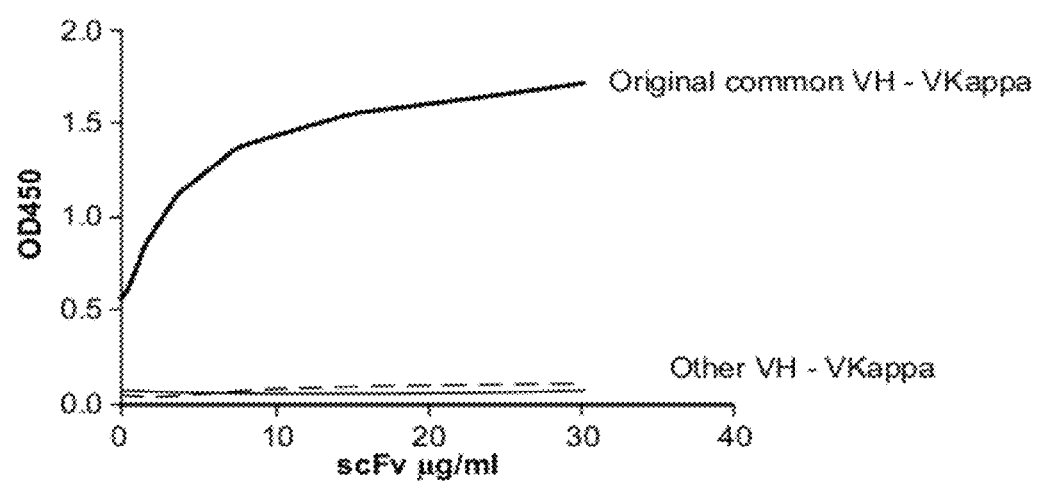

In order to test the contribution of the common VH to antigen binding, different light chains of scFv bearing a common VH selected in Example 1 and 4, were combined with two different VH that are different for the original common VH. The different scFv could be expressed and purified as described in Example 3 and tested for binding against the target against which they had been selected. Examples shown in FIG. 21 show that a scFv specific for INFγ and a scFv specific against IL6RC can only bind to their respective targets when combined with the VH domain with which they been originally selected and no binding is observed when combined with two other VH domain that allow for their expression and purification. The results indicate that despite the fact that diversity is restricted to the VL domain, both the common VH and the VL contribute to antigen binding.

Example 15

Development of ELISA for IgGκλ Bispecific Antibody Quantification

A sandwich ELISA to quantify IgGκλ bispecific antibodies was developed. 96-well Maxisorp (Nunc) plates were coated with 10 ug/ml mouse anti human Lambda antibody (Southern Biotech) and incubated at 4° C. overnight. After washing (PBS Tween 20 at 0.05%, 3 washes), plate was blocked with PBS-BSA 3% (Sigma) for 2 hours at room temperature. Purified IgGκλ standard was serially diluted in PBS-BSA 1% between 500 ng/ml and 1 ng/ml to obtain a good linearity range for sample quantification. Depending on their origin the samples were diluted to enter the quantification range as follow: Crude CHO supernatant 1/1500; Protein A purified 1/15000. The samples were then diluted serially 1:2. After washing of the plates, 50 ul of each prepared dilution was added in duplicate and incubated for 1 hour at room temperature. Plates were washed again and incubated for 1 hour at room temperature with 50 ul of 1:2000 anti human Kappa antibody (Southern Biotech). After the last wash (PBST 0.05%, 5 washes), the reaction was revealed with 50 ul of TMB substrate (Sigma) and stopped after 15 min by adding 50 ul of H2SO4 (Sodium hydroxide 2N). The absorbance at 450 nm was recorded using a precision microplate reader (Epoch, Witec). As the monospecific antibodies might affect the assay by binding to coated capture antibody, spiking experiments were performed by adding increasing amounts of monospecific IgGκ and monospecific IgGλ antibodies to the IgGκλ bispecific standard. Different ratios were tested: (50% IgGκλ bispecific, 25% monospecific IgGκ, 25% monospecific IgGλ); (67% IgGκλ bispecific; 33% monospecific IgGλ); (50% IgGκλ bispecific, 50% monospecific IgGλ); (25% IgGκλ bispecific, 75% monospecific IgGλ); (50% IgGκλ bispecific, 50% monospecific IgGκ).

Figure 22:
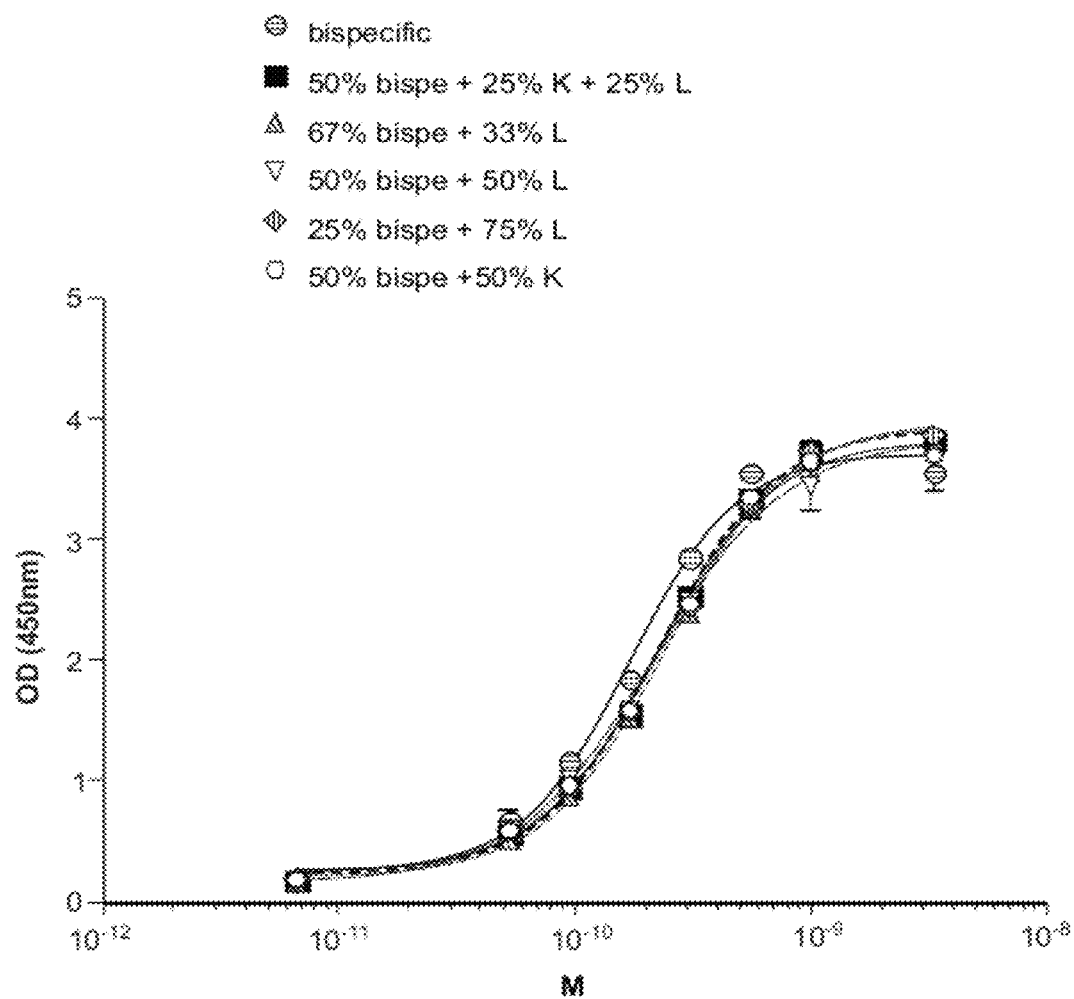
FIG. 22 is a graph depicting the results obtained for IgGκλ bispecific antibody quantification using a sandwich ELISA format. The dose response was performed using either purified bispecific antibody alone or mixed with monospecific Kappa or Lambda antibodies at different ratios as indicated, in order to evaluate the interference of these molecules in the assay.

The results shown in FIG. 22 indicate that the assay is not affected significantly by monospecific antibodies and that therefore it can be used for IgGκλ bispecific antibody quantification in complex samples such cell culture supernatants. The ELISA was used to quantify IgGκλ bispecific antibody in supernatant from stable CHO cell lines and after total IgG purified from the same supernatants by Protein A affinity chromatography. The ELISA quantification results were compared to total IgG content determined by Protein A HPLC or by absorption at 280 nm and are summarized in Table V. The concentrations obtained by ELISA corresponded to 30-40% of total IgG, a proportion of bispecific that is expected. The data shows that this assay can be used to determine the amount of IgGκλ bispecific antibody in a cell culture supernatant and facilitates the screening of stable cell lines for their productivity in IgGκλ bispecific antibody.

TABLE V

IgGκλ bispecific antibody quantification for different stable CHO cell lines using crude supernatants or total IgG by ELISA and compared to ProteinA HPLC and A280 quantification results of total IgG.

| Cell line | CHO supernatants | | Protein A purified Tot IgG | |
|---|---|---|---|---|
| | Prot A HPLC | ELISA | A280 nm | ELISA |
| #11 | 0.3 mg/ml | 0.18 mg/ml | 4.38 mg/ml | 2.3 mg/ml |
| #14 | 0.42 mg/ml | 0.234 mg/ml | 4.13 mg/ml | 3.3 mg/ml |
| #20 | 0.38 mg/ml | 0.18 mg/ml | 4.48 mg/ml | 1.7 mg/ml |
| 10E4 | 0.39 mg/ml | 0.19 mg/ml | 4.81 mg/ml | 3 mg/ml |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated bispecific antibody carrying a different specificity in each of a first combining site and a second combining site and consisting of two copies of a single heavy chain polypeptide and a first light chain and a second light chain, wherein the first and second light chains are different, wherein the first light chain comprises a Kappa constant region and a Kappa variable region, wherein the second light chain comprises a Lambda constant region and a Lambda variable region, and wherein the first combining site specifically binds to a first antigen and the second combining site specifically binds to a second antigen.

2. The isolated bispecific antibody of claim 1, wherein the constant and variable framework region sequences are human.

* * * * *